(12) United States Patent
Scianamblo

(10) Patent No.: US 6,942,484 B2
(45) Date of Patent: Sep. 13, 2005

(54) CRITICAL PATH ENDODONTIC INSTRUMENTS FOR PREPARING ENDODONTIC CAVITY SPACES

(76) Inventor: Michael J. Scianamblo, 1526 Fifth Ave., San Rafael, CA (US) 94901

( * ) Notice: Subject to any disclaimer, the term of this patent is extended or adjusted under 35 U.S.C. 154(b) by 0 days.

(21) Appl. No.: 10/838,399

(22) Filed: May 3, 2004

(65) Prior Publication Data

US 2004/0219485 A1 Nov. 4, 2004

Related U.S. Application Data

(63) Continuation-in-part of application No. 10/764,337, filed on Jan. 22, 2004.
(60) Provisional application No. 60/477,688, filed on Jun. 10, 2003, and provisional application No. 60/467,472, filed on May 1, 2003.

(51) Int. Cl.[7] .................................................. A61C 5/02
(52) U.S. Cl. ...................................................... 433/102
(58) Field of Search ................................. 433/102, 224, 433/165

(56) References Cited

U.S. PATENT DOCUMENTS

| | | | |
|---|---|---|---|
| 4,353,698 A | 10/1982 | McSpadden | 433/164 |
| 4,457,710 A | 7/1984 | McSpadden | 433/81 |
| 4,992,048 A | * 2/1991 | Goof | 433/102 |
| 5,503,554 A | * 4/1996 | Schoeffel | 433/102 |
| 5,605,460 A | * 2/1997 | Heath et al. | 433/224 |
| 5,676,541 A | * 10/1997 | Maillefer et al. | 433/102 |
| 5,882,198 A | 3/1999 | Taylor et al. | 433/102 |
| 5,902,106 A | 5/1999 | McSpadden | 433/102 |
| 5,938,440 A | 8/1999 | McSpadden | 433/102 |

\* cited by examiner

*Primary Examiner*—Cary E. O'Connor
(74) *Attorney, Agent, or Firm*—Fish & Richardson P.C.

(57) ABSTRACT

Methods and apparatus providing a critical set of endodontic instruments. The set includes a first endodontic instrument, a second endodontic instrument, and a third endodontic instrument. Each endodontic instrument includes a working portion that has a cone-like shape. Each working portion having an effective contact area defined by the exposed surface area of the working portion's respective cone-like shape. The difference between the effective contact areas of the first endodontic instrument and second endodontic instrument being substantially the same as the difference between the effective contact areas of the second endodontic instrument and third endodontic instrument.

19 Claims, 21 Drawing Sheets

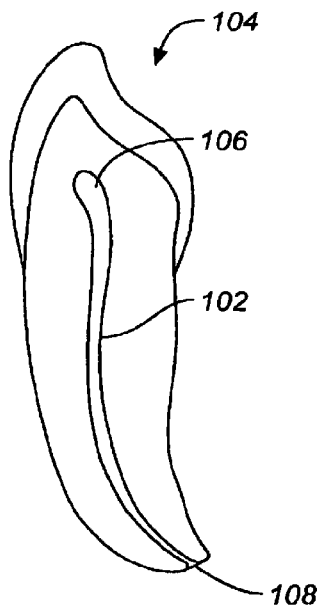
FIG._1A
*(PRIOR ART)*
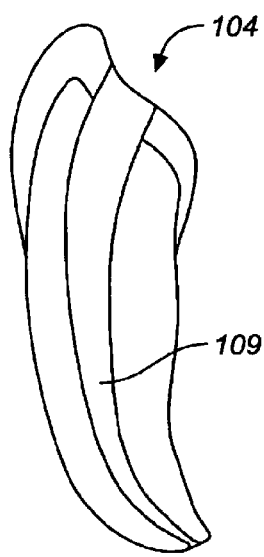
FIG._1B
*(PRIOR ART)*
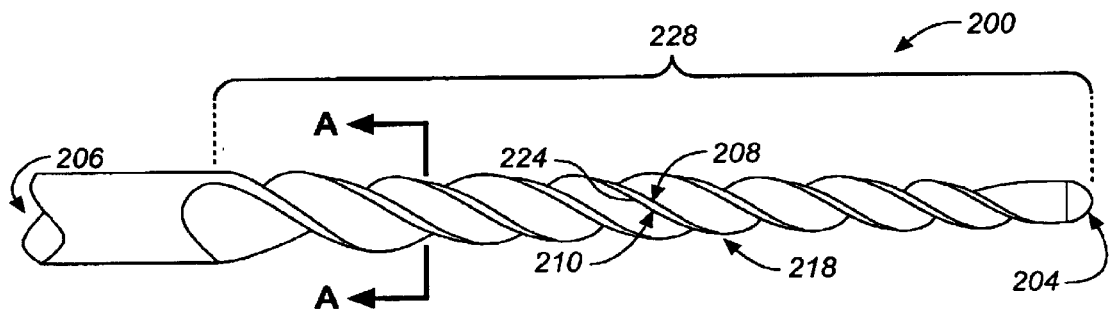
FIG._2A *(PRIOR ART)*
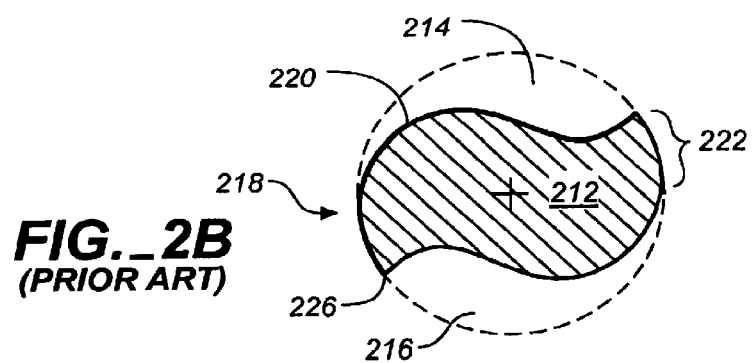
FIG._2B *(PRIOR ART)*

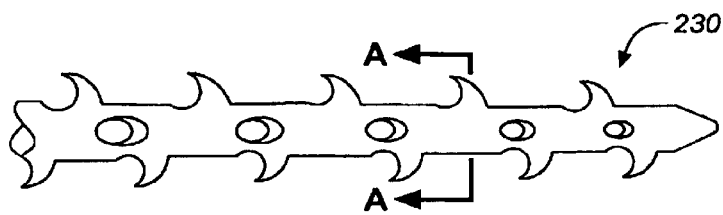
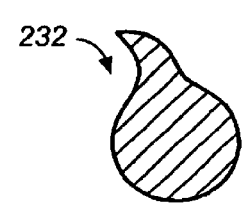
FIG._2C (PRIOR ART)     FIG._2D (PRIOR ART)
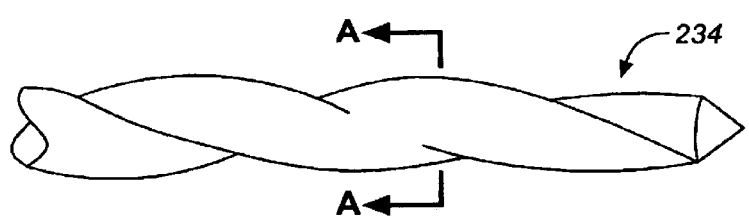
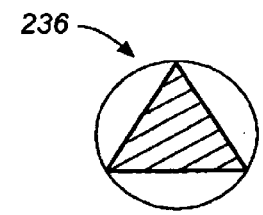
FIG._2E (PRIOR ART)     FIG._2F (PRIOR ART)
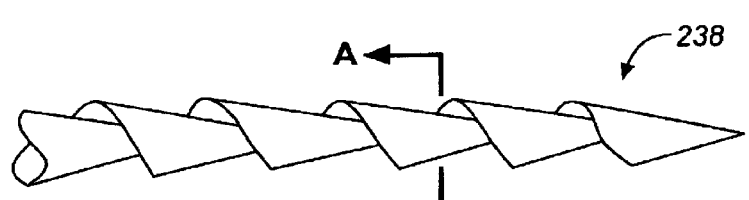
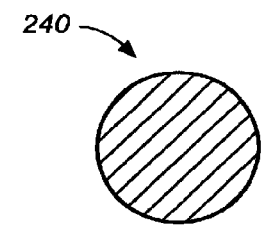
FIG._2G (PRIOR ART)     FIG._2H (PRIOR ART)
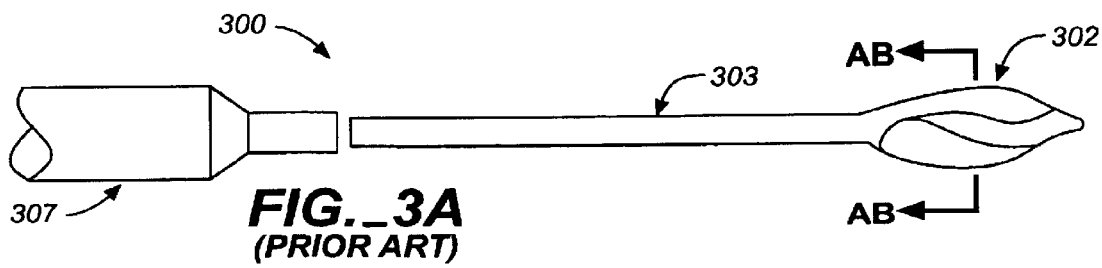
FIG._3A (PRIOR ART)
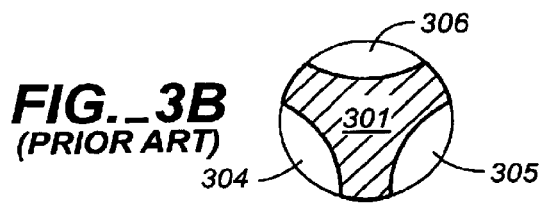
FIG._3B (PRIOR ART)

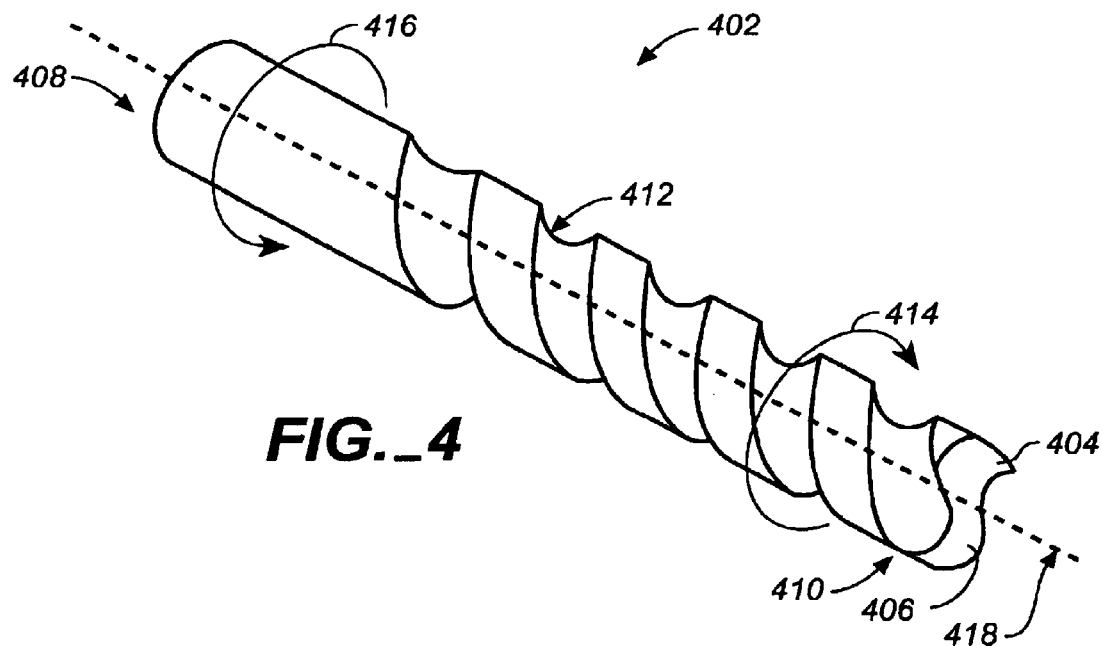
FIG._4
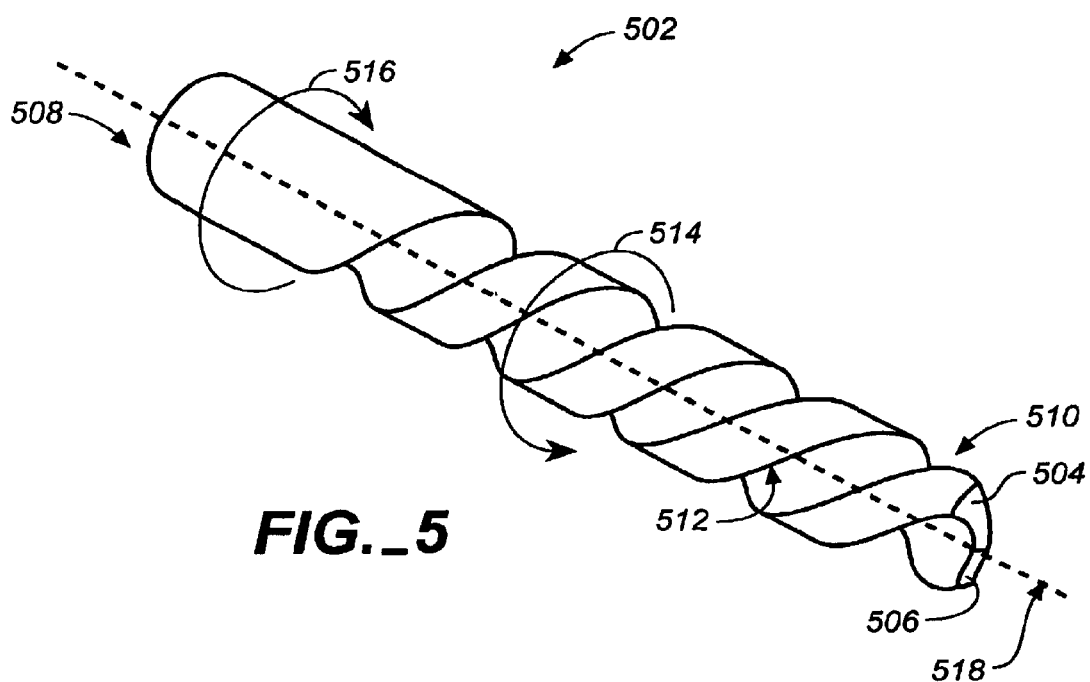
FIG._5

 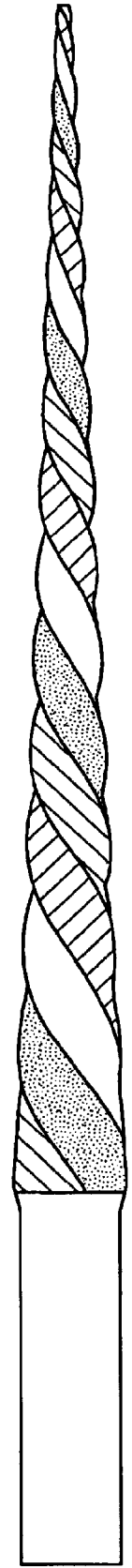
FIG._6A  FIG._6B

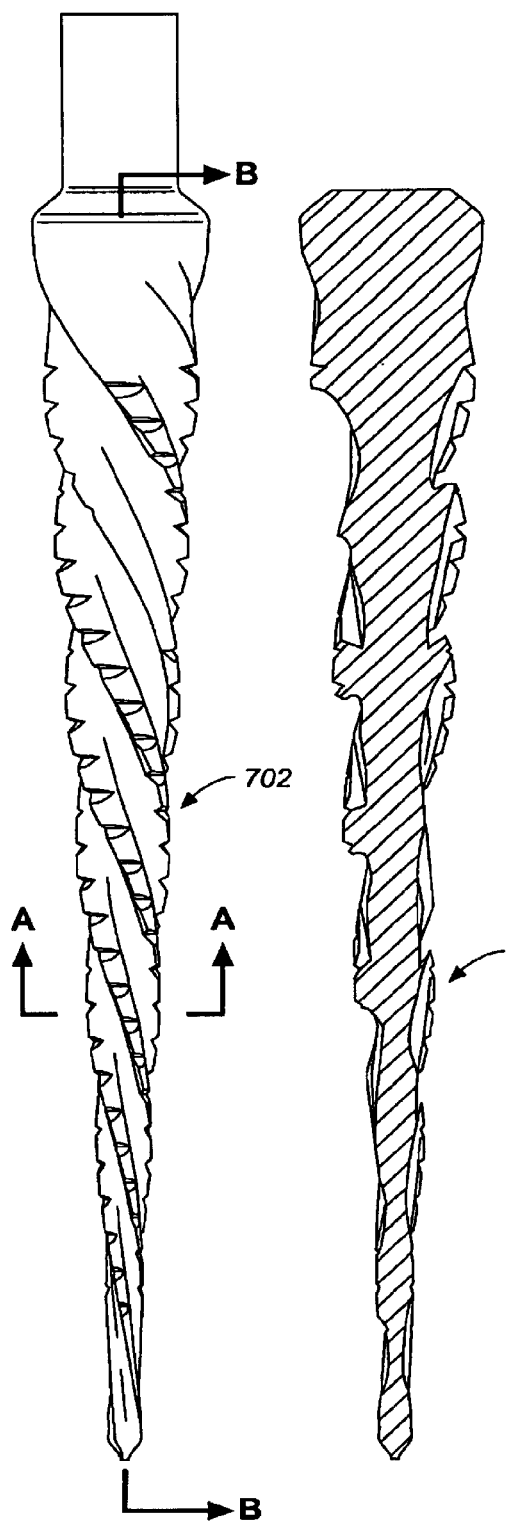
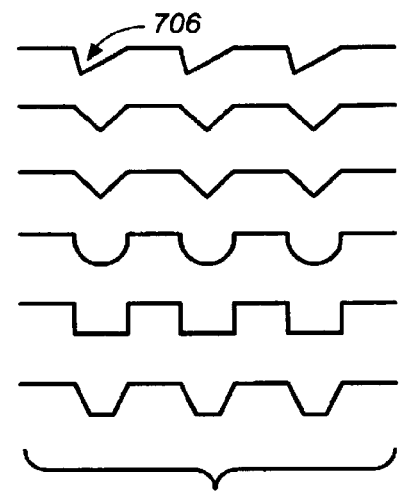
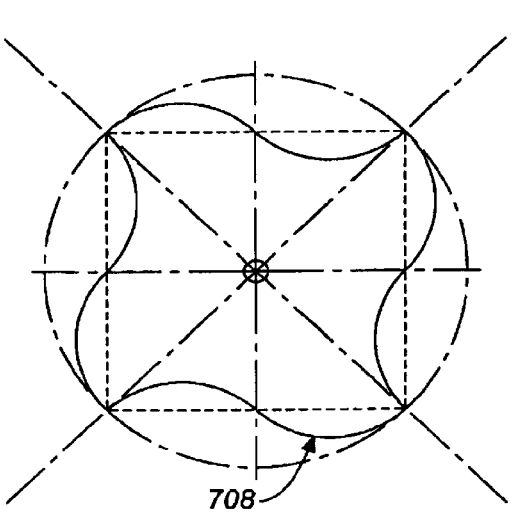
FIG._7A  FIG._7B  FIG._7C  FIG._7D

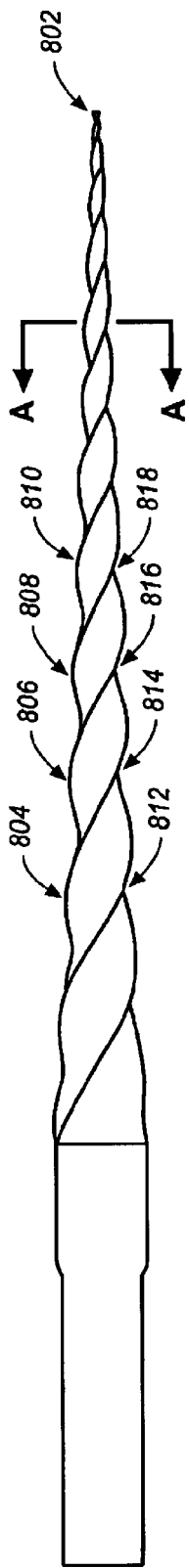
FIG._8A
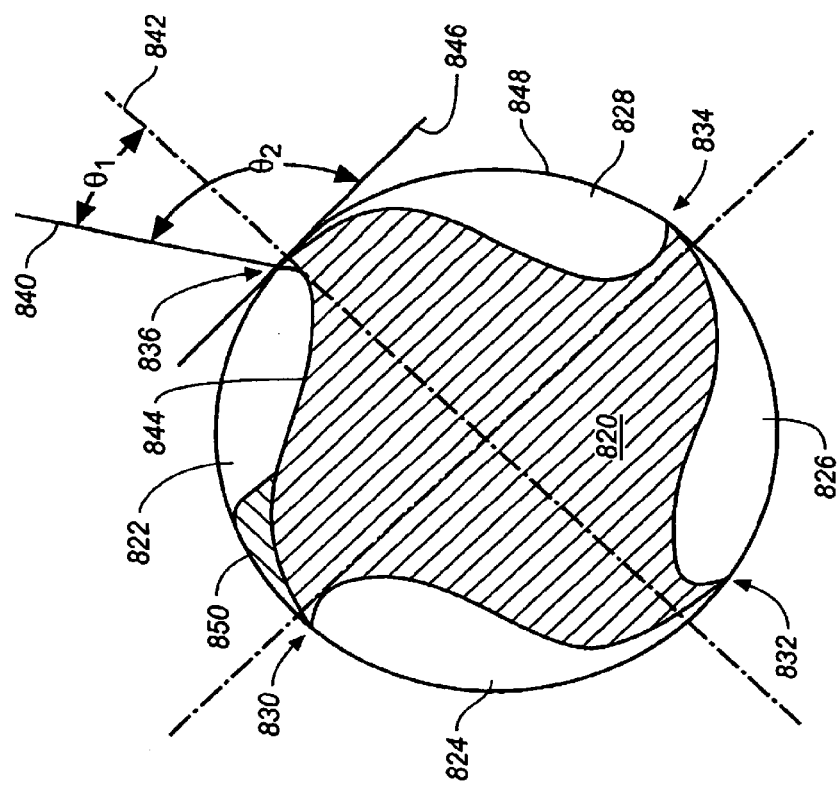
FIG._8B

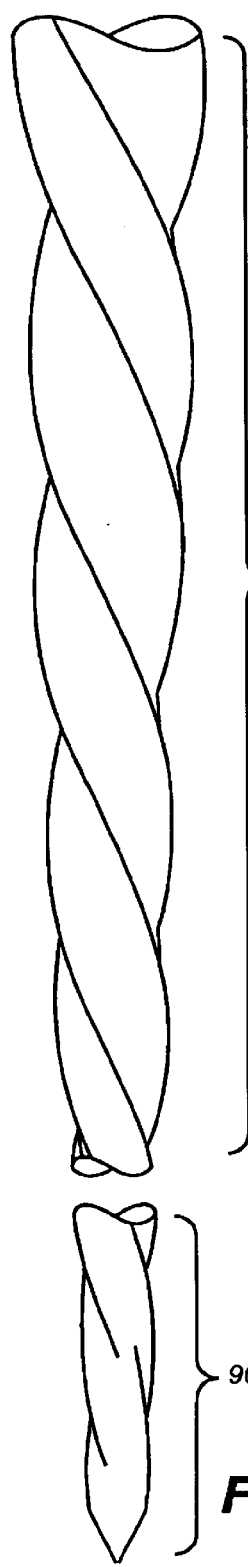
FIG._9B
FIG._9A  FIG._9C  FIG._9D

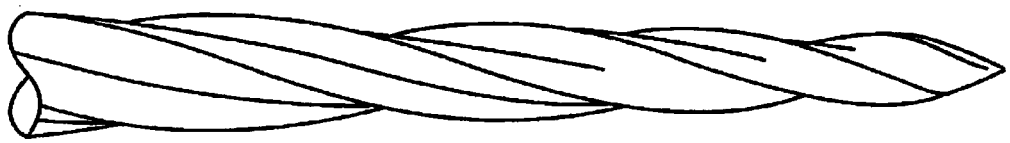
FIG._9E
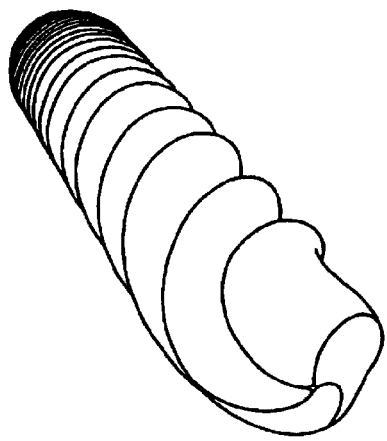
FIG._9F
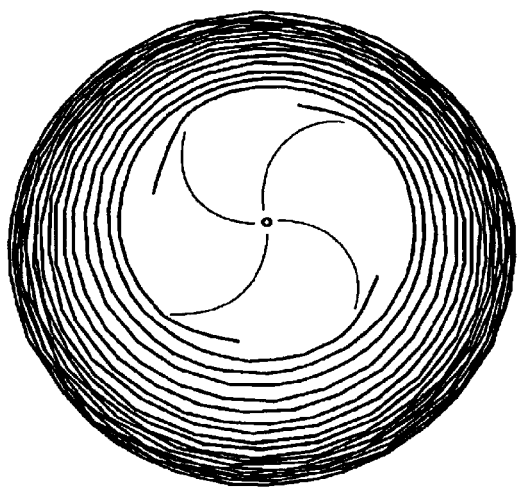
FIG._9G
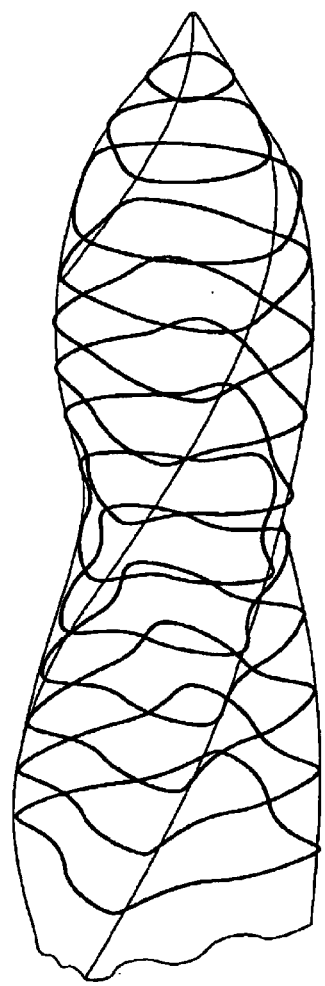
FIG._9H

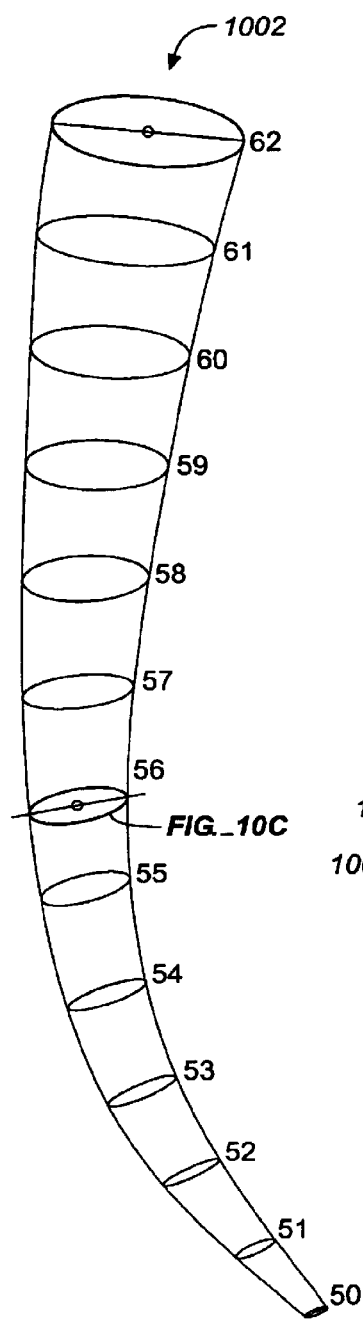
FIG._10B
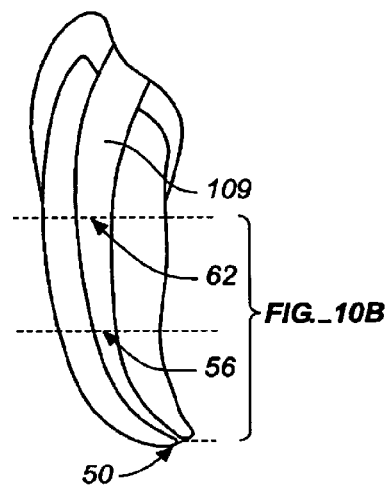
FIG._10A
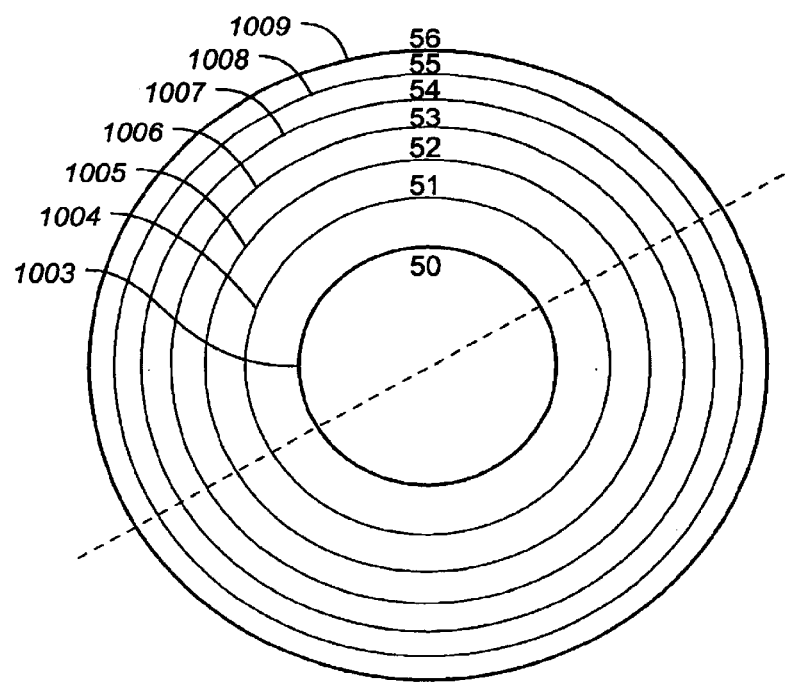
FIG._10C

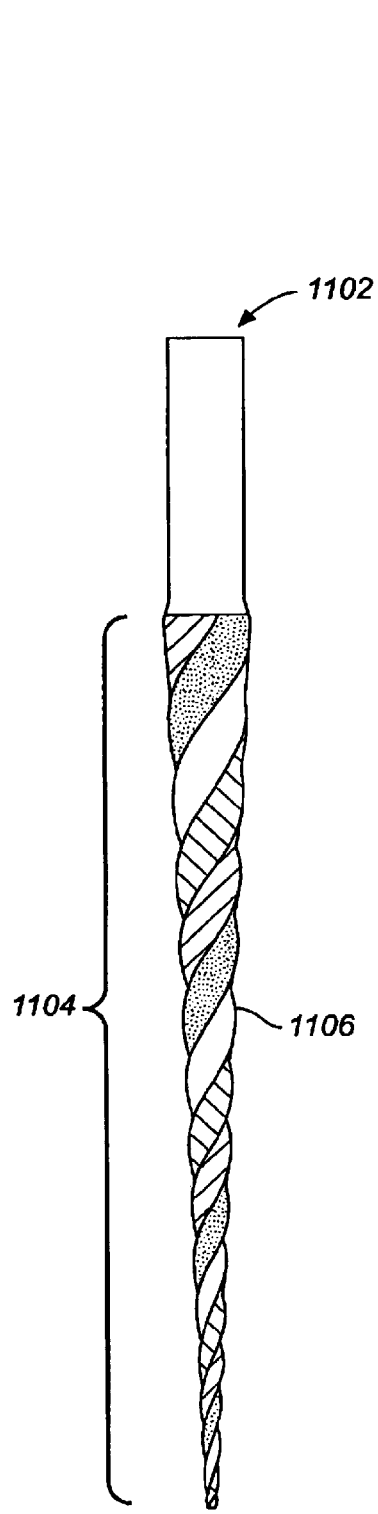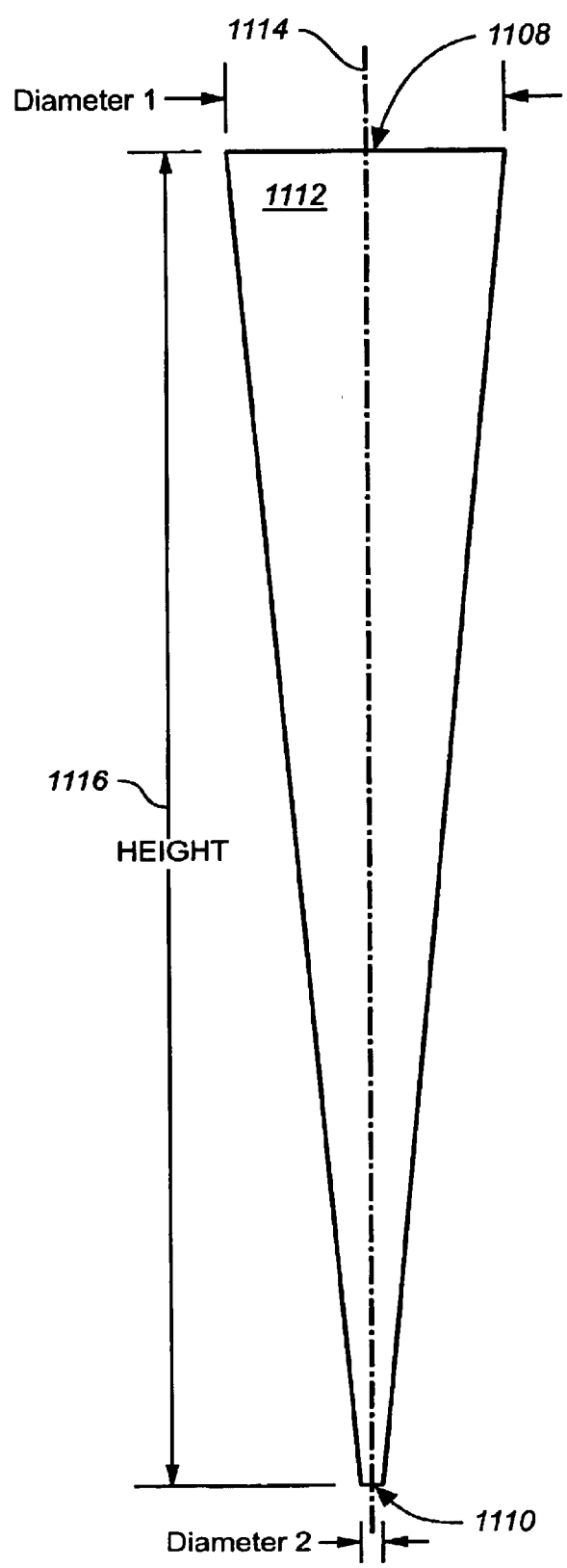
FIG._11A   FIG._11B

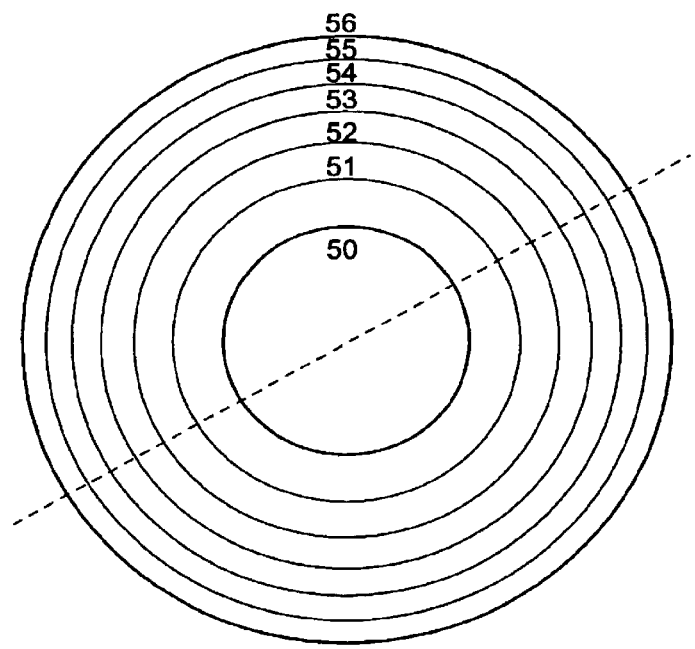
FIG._11C
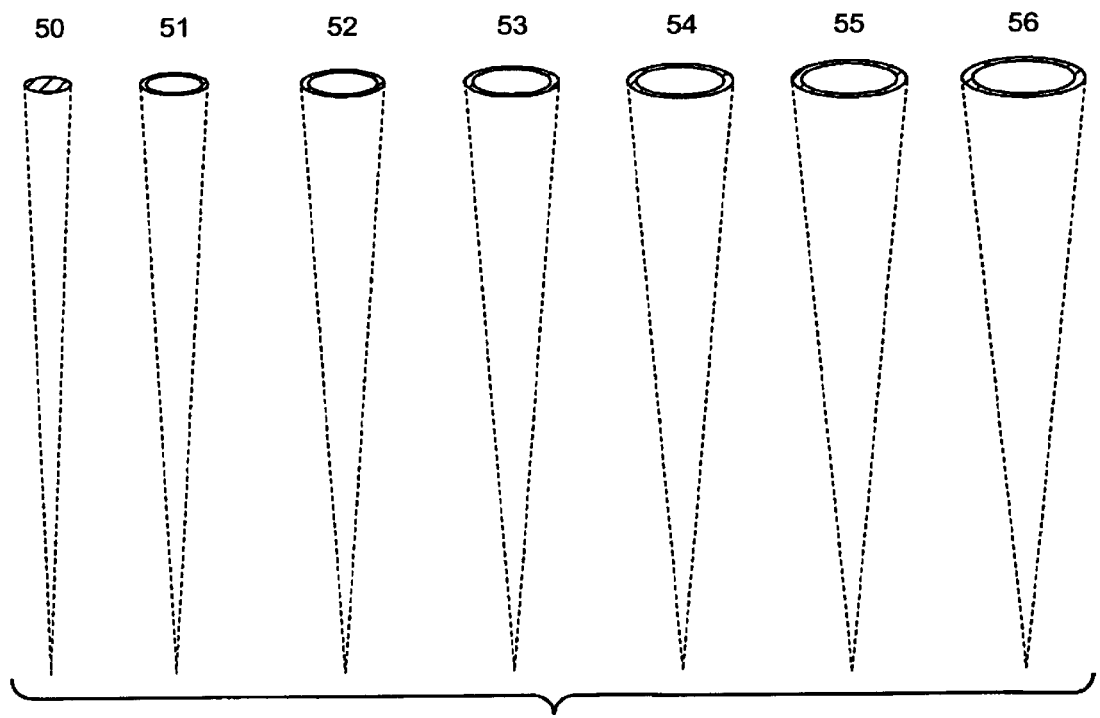
FIG._11D

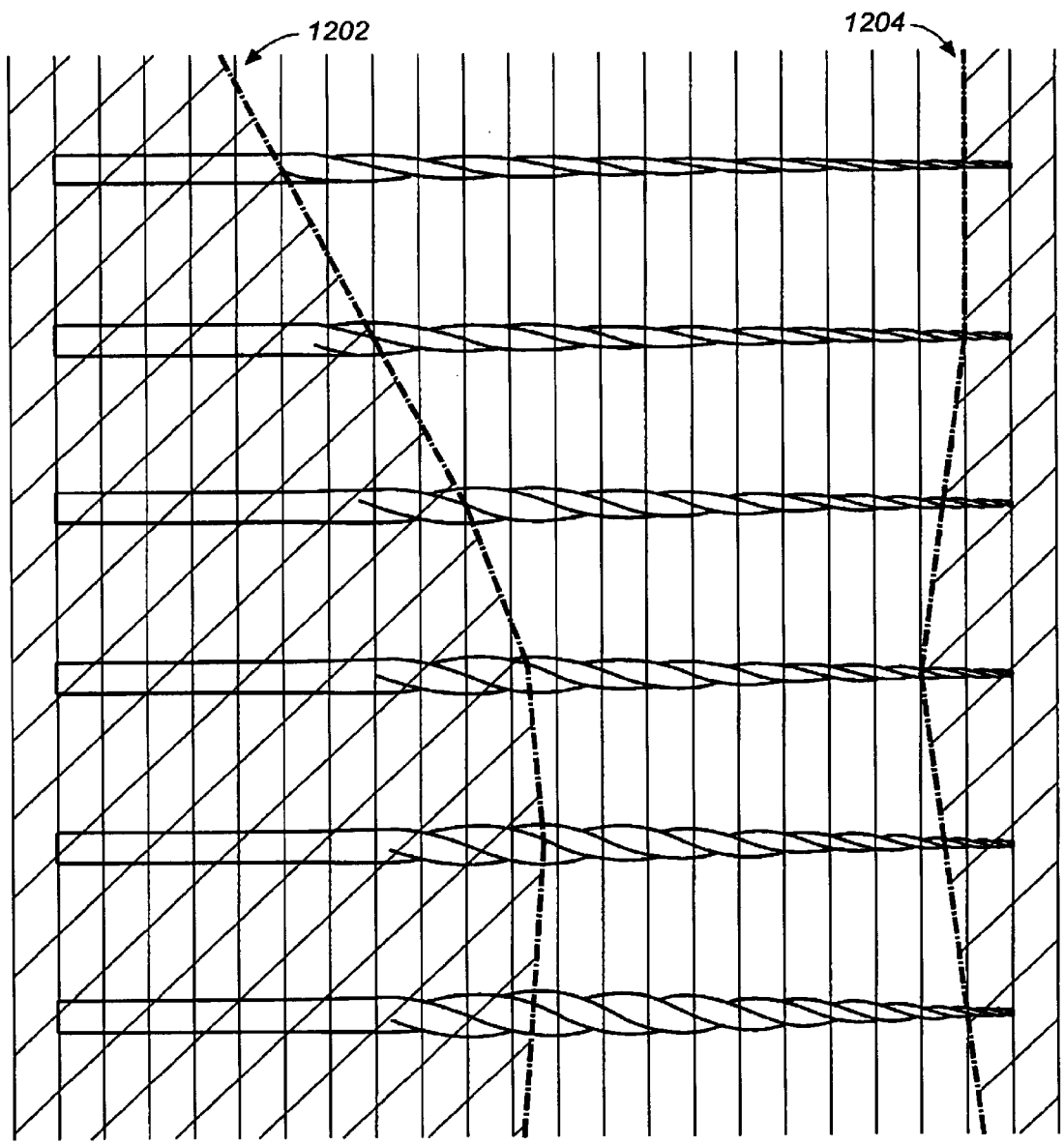
FIG._12

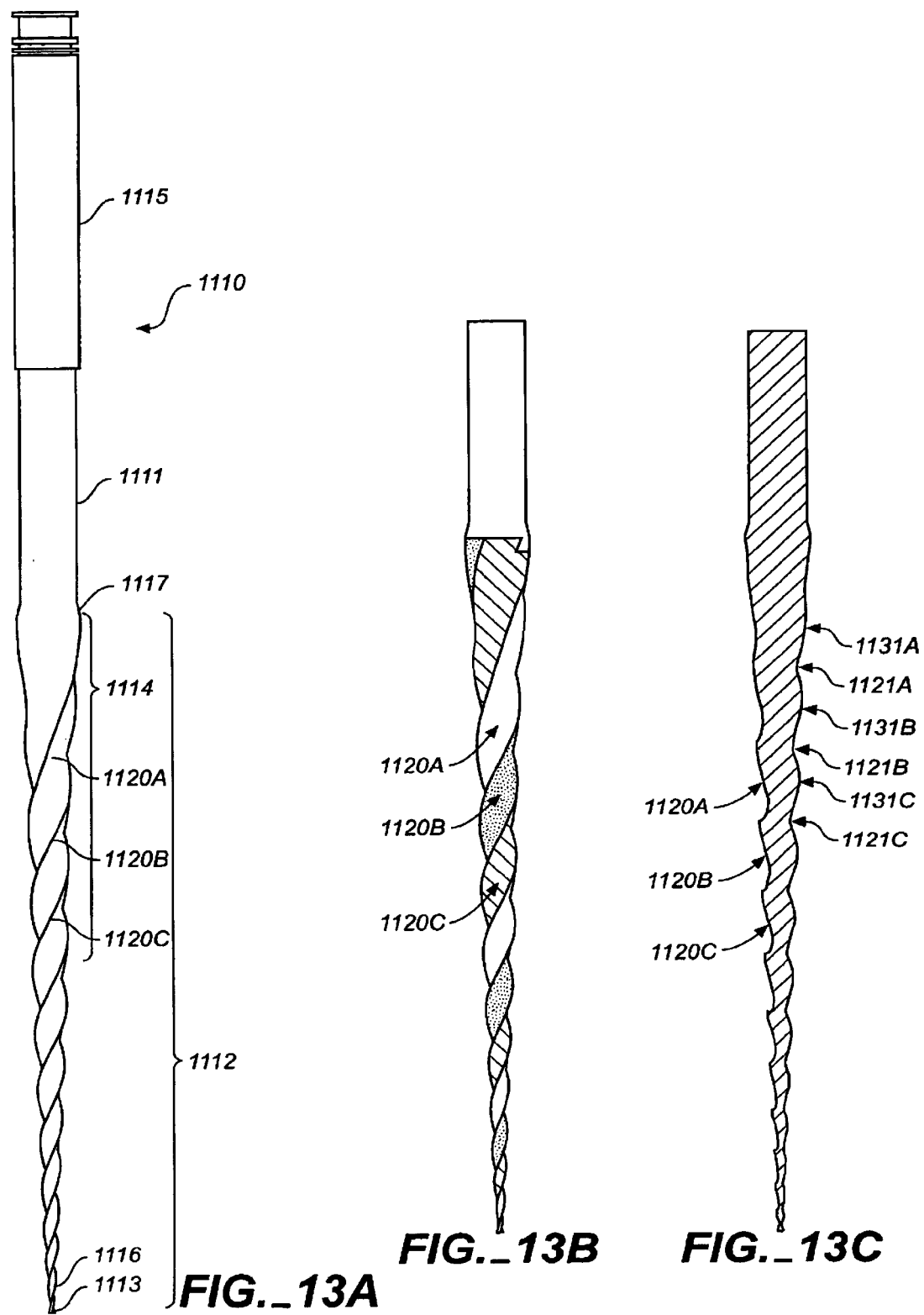

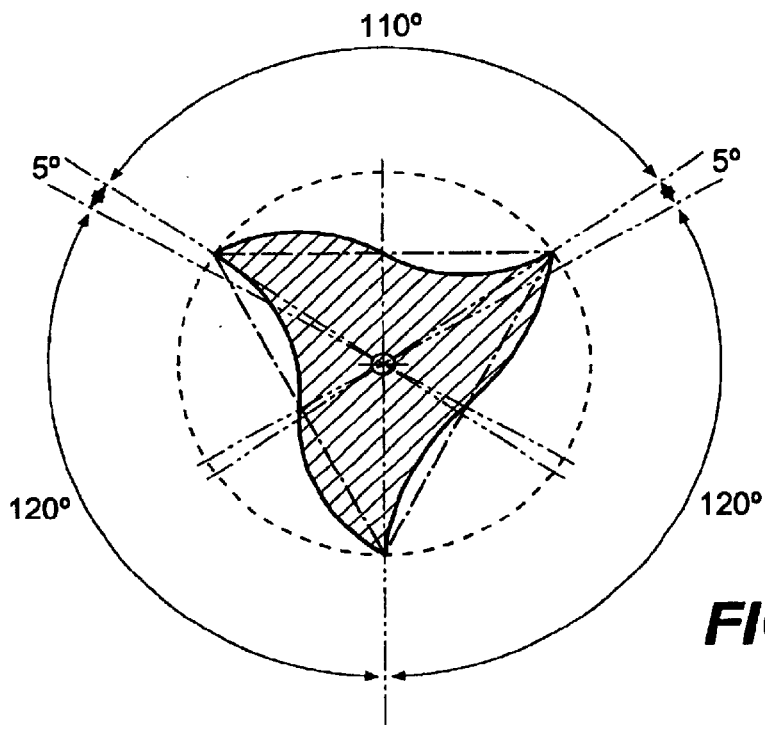
FIG._13D
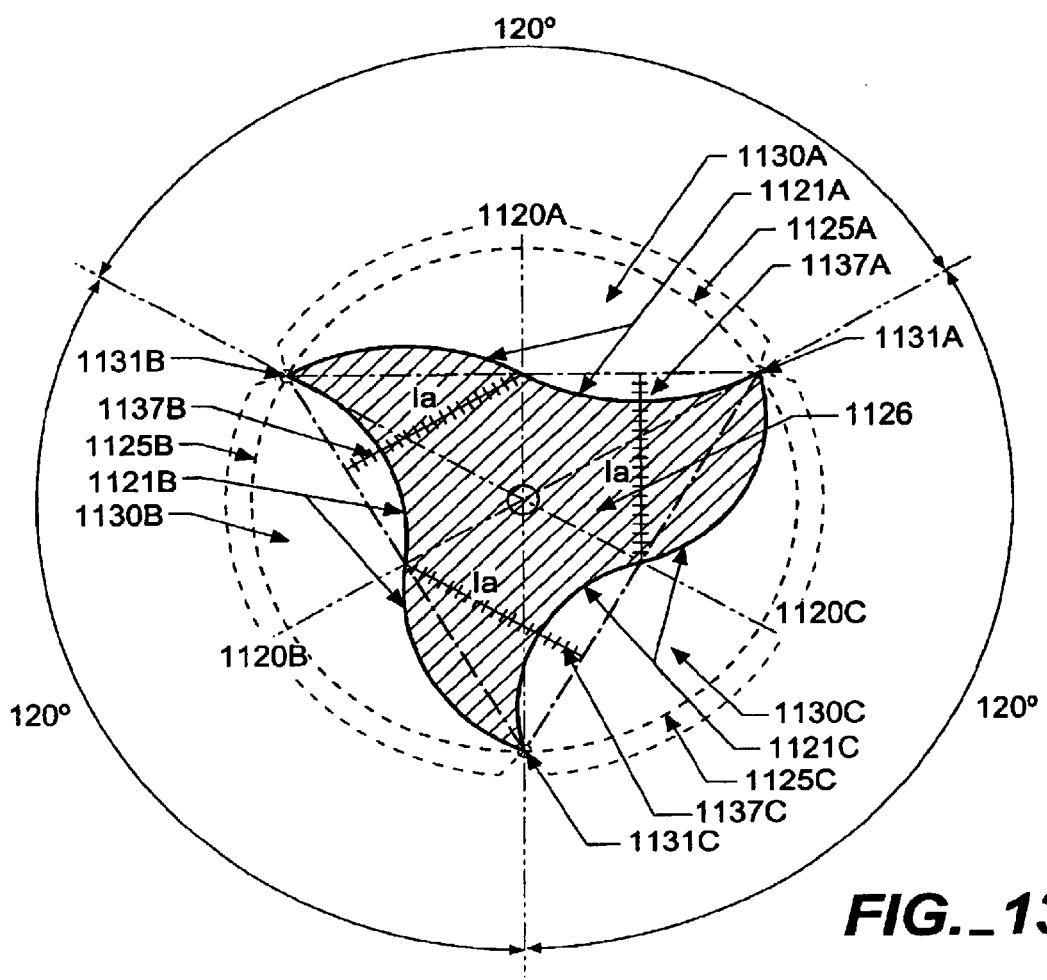
FIG._13E

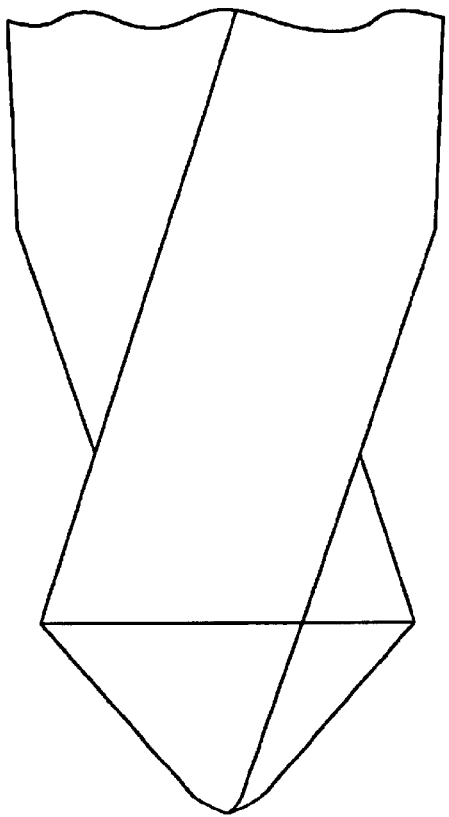
FIG._14A
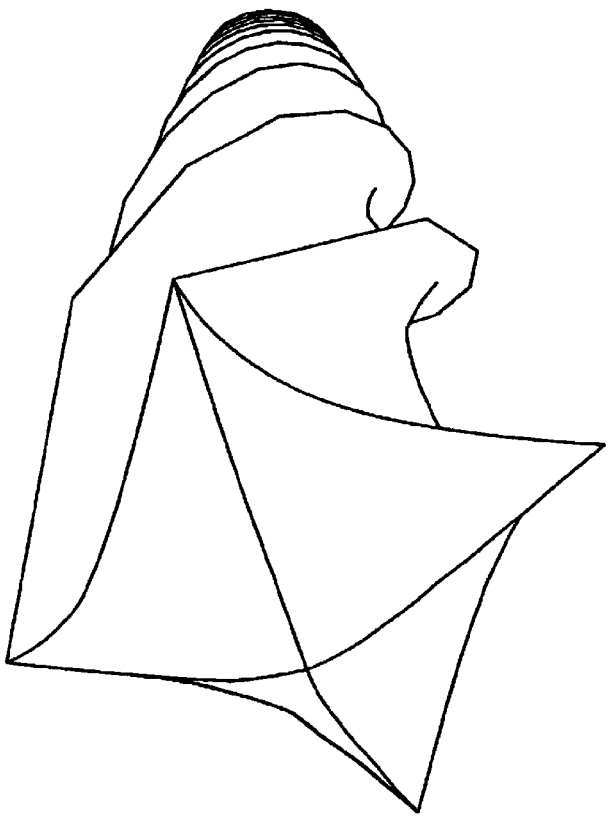
FIG._14D
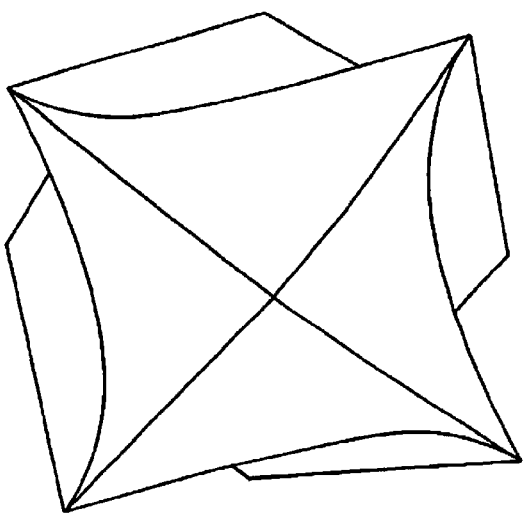
FIG._14B
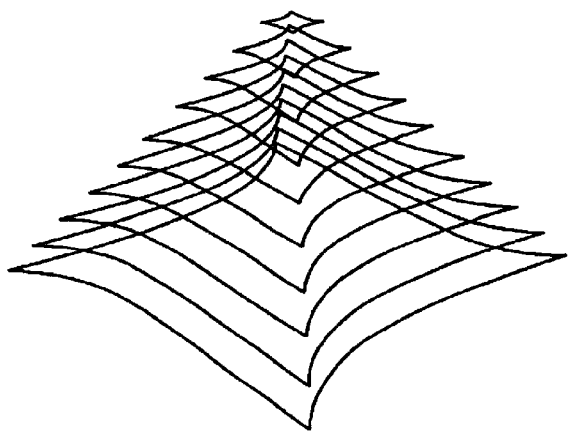
FIG._14C

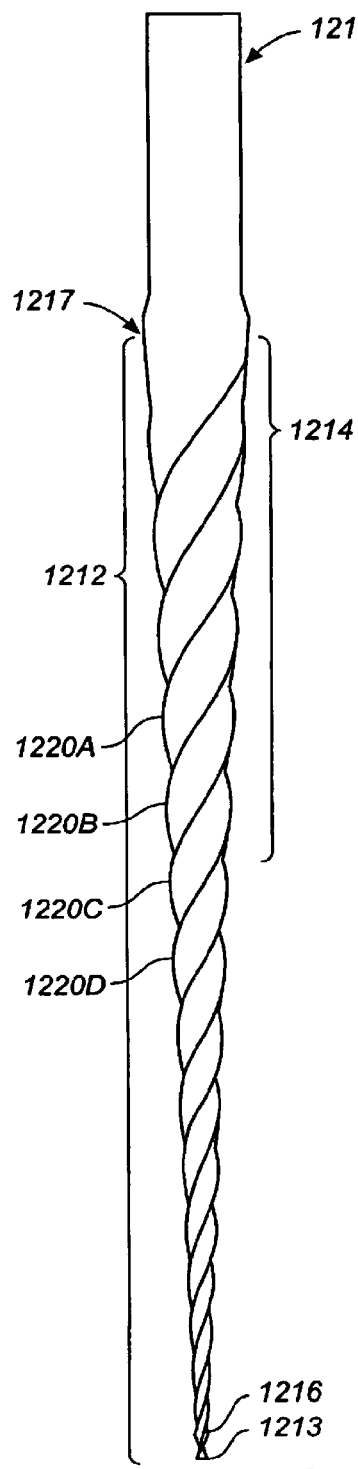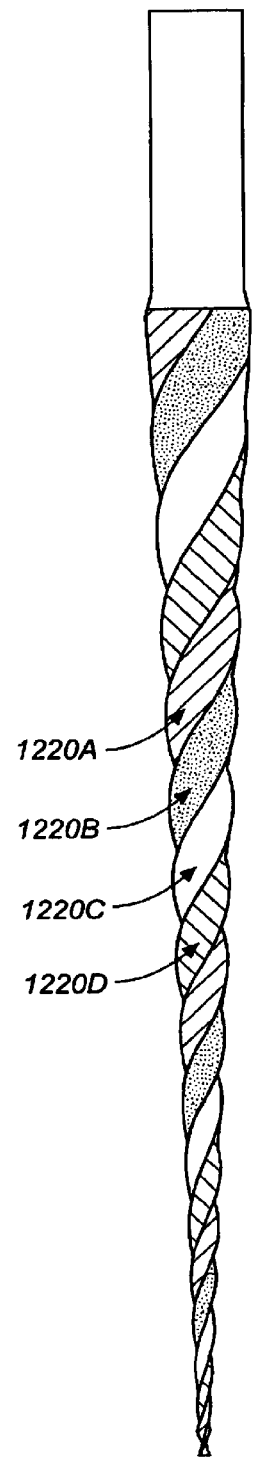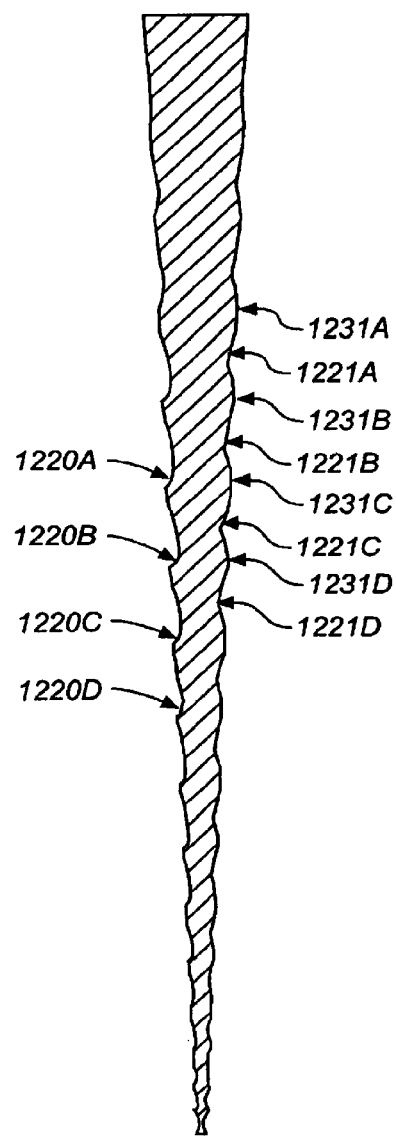
FIG._15A　　FIG._15B　　FIG._15C

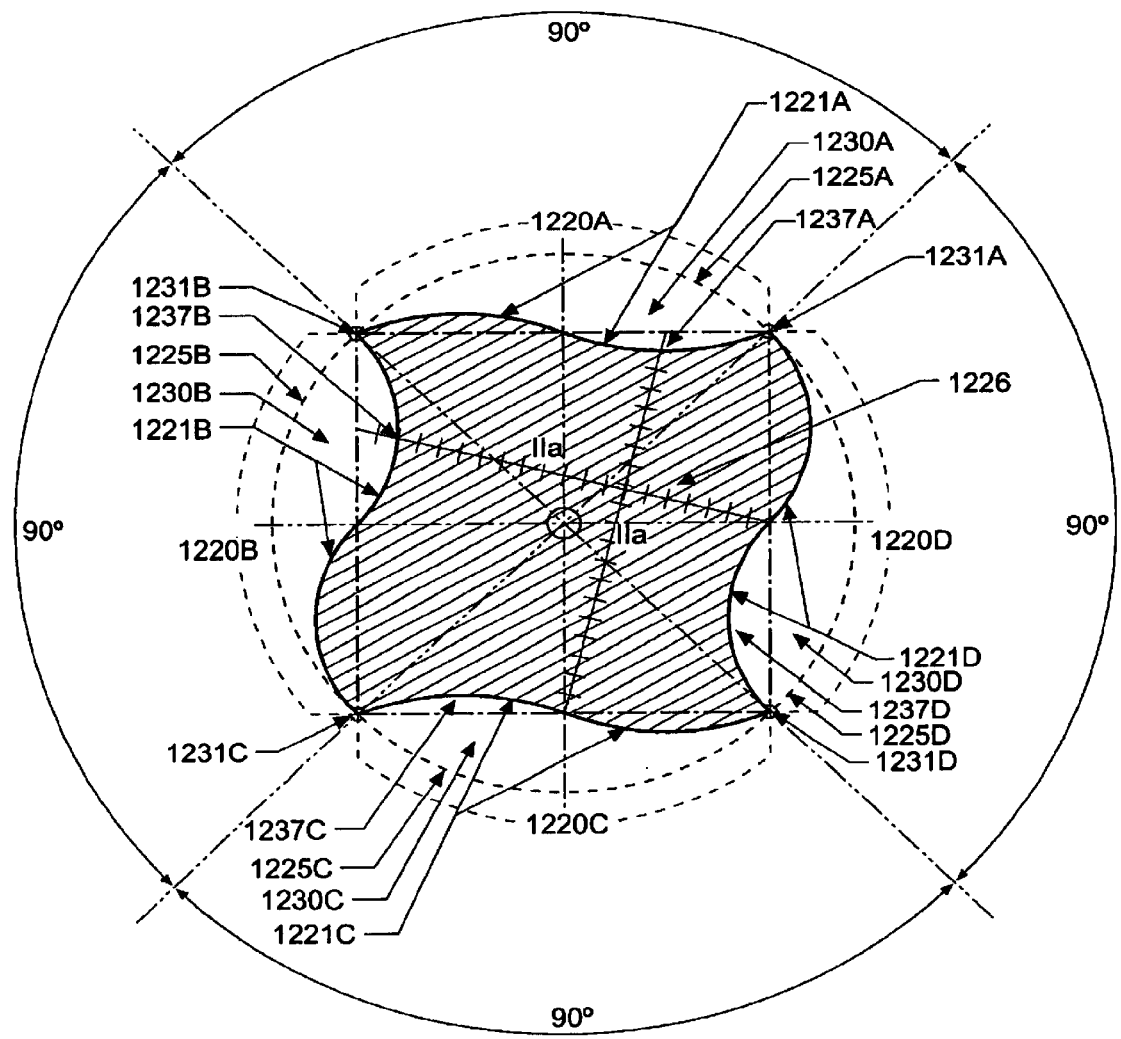
FIG._15D

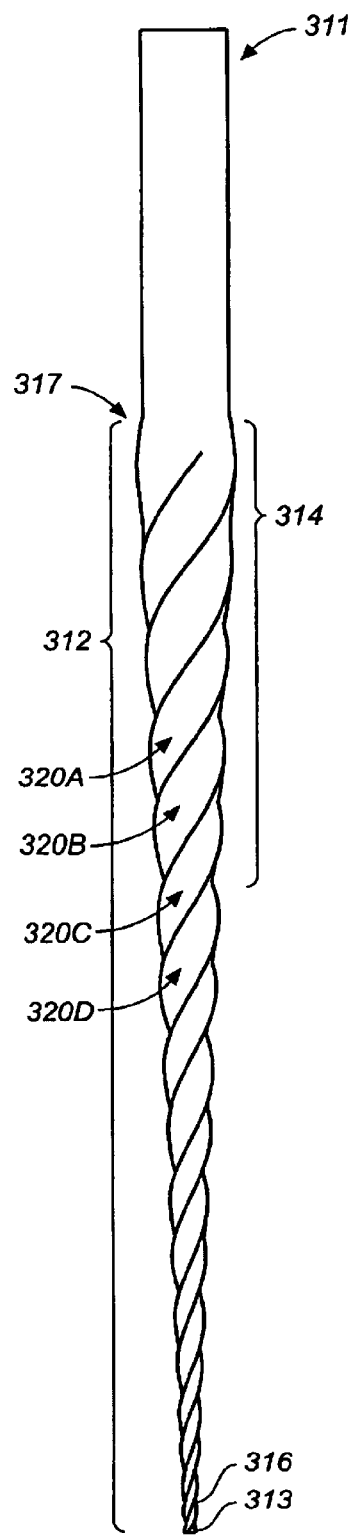
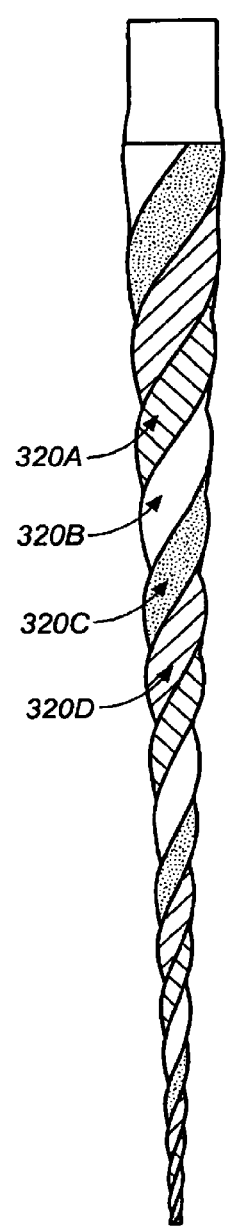
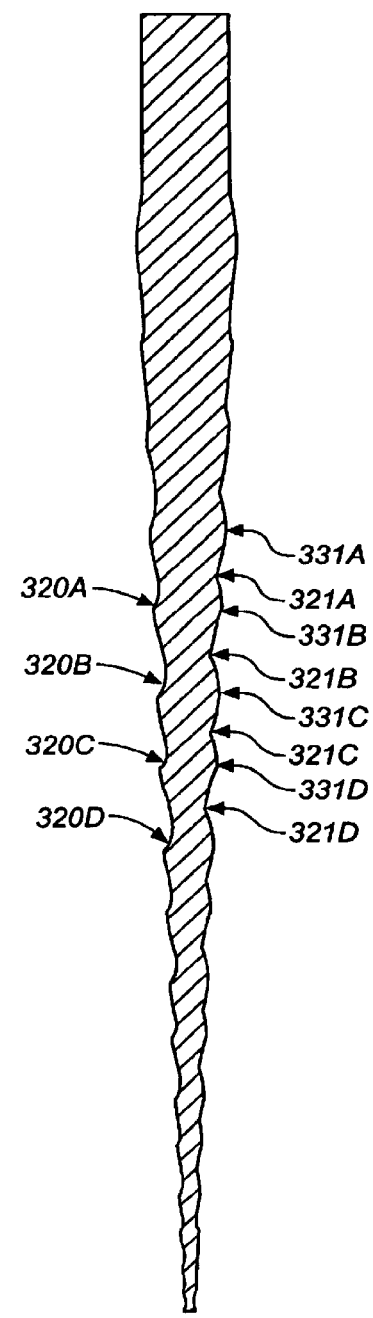
*FIG._16A*  *FIG._16B*  *FIG._16C*

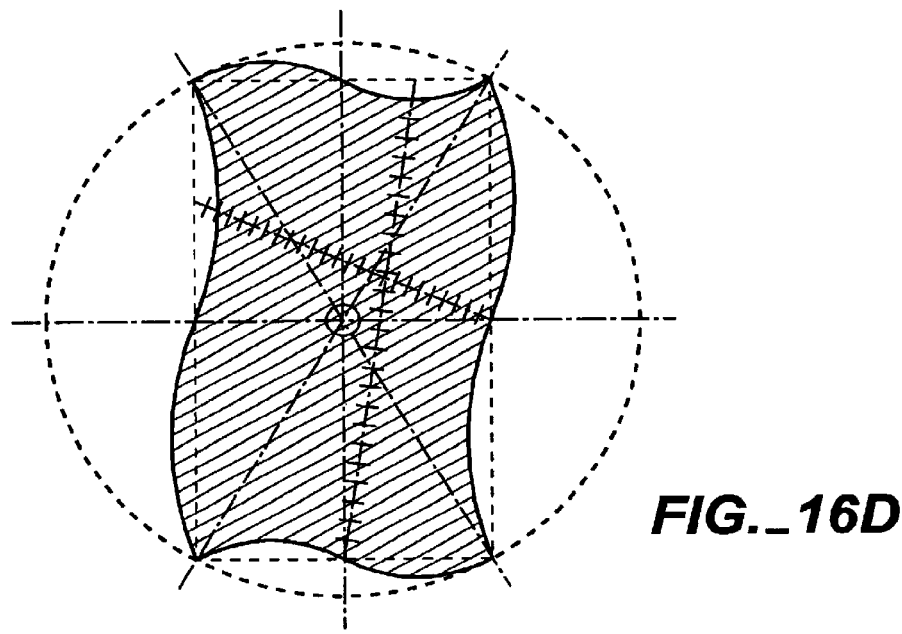
FIG._16D
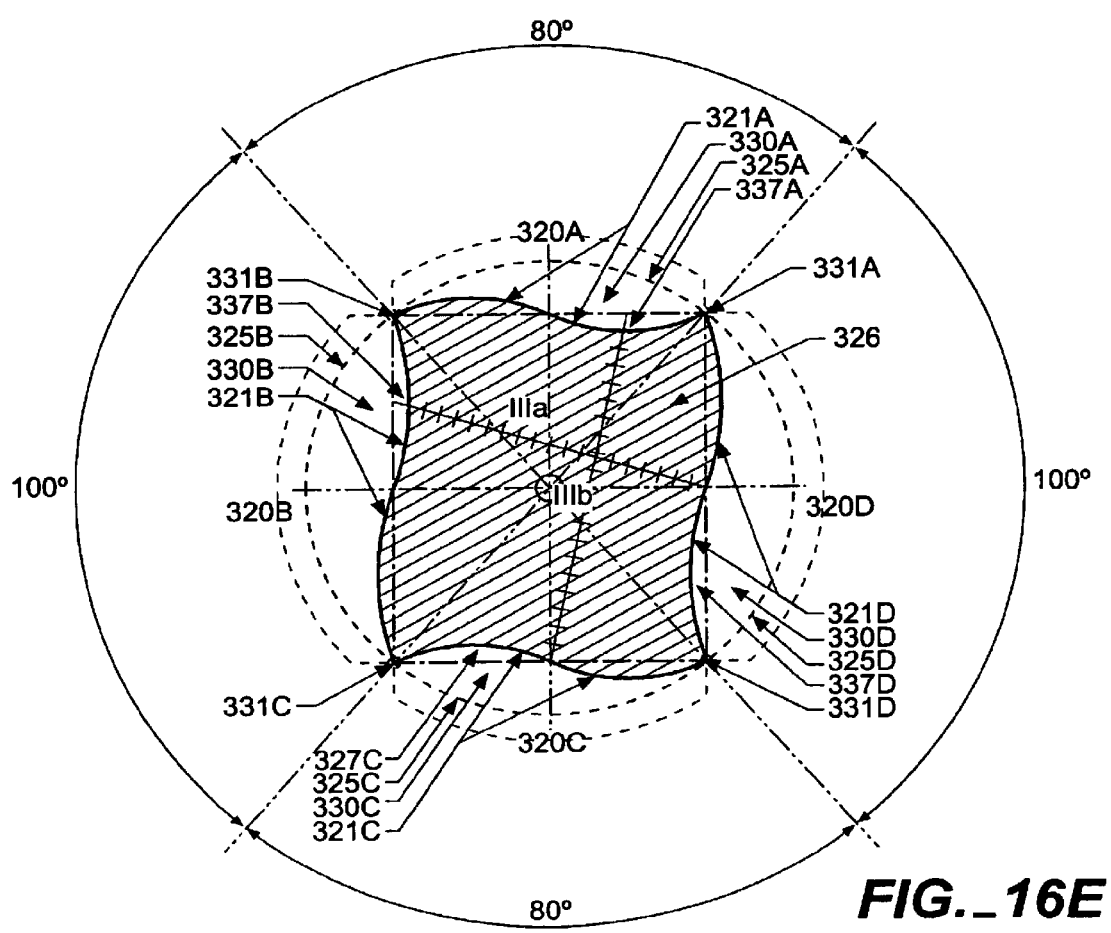
FIG._16E

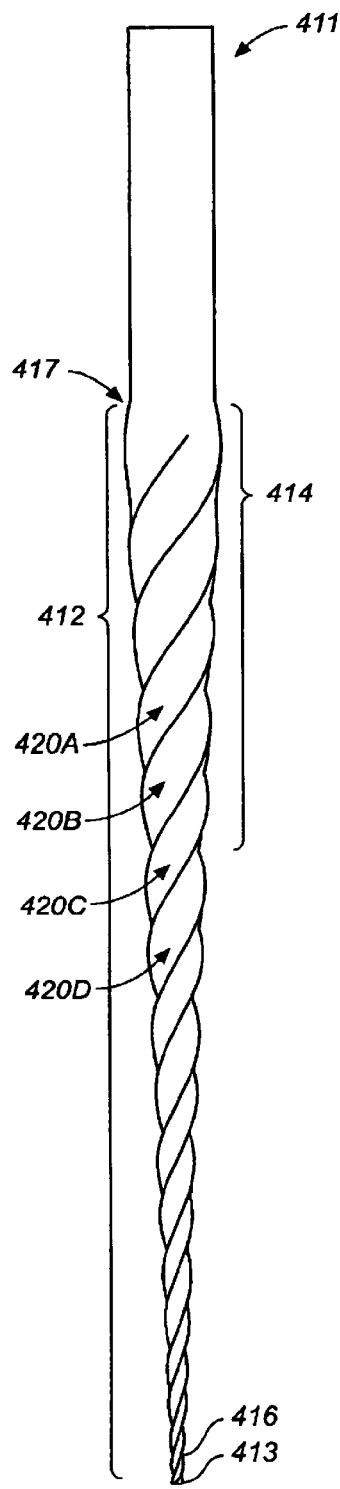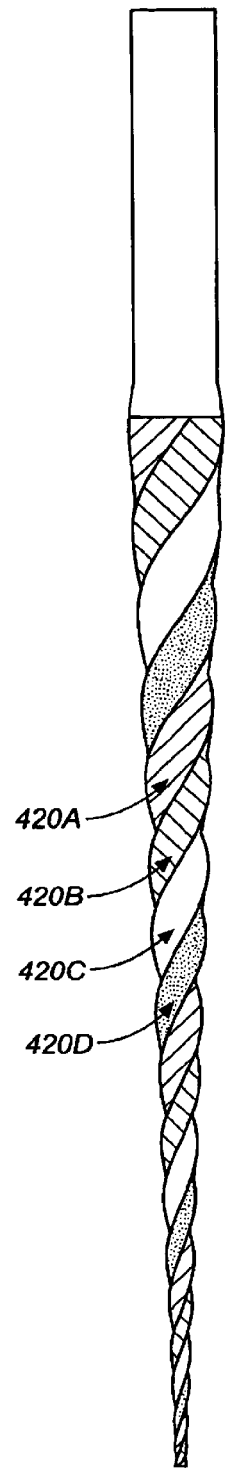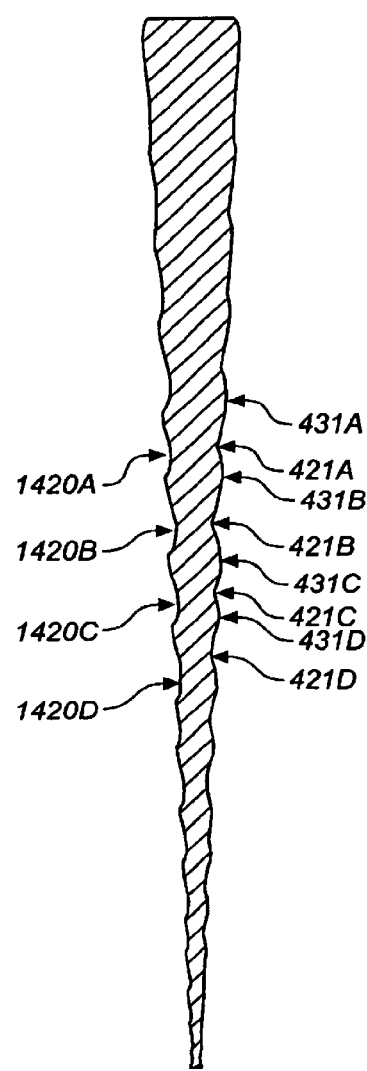
*FIG._17A*  *FIG._17B*  *FIG._17C*

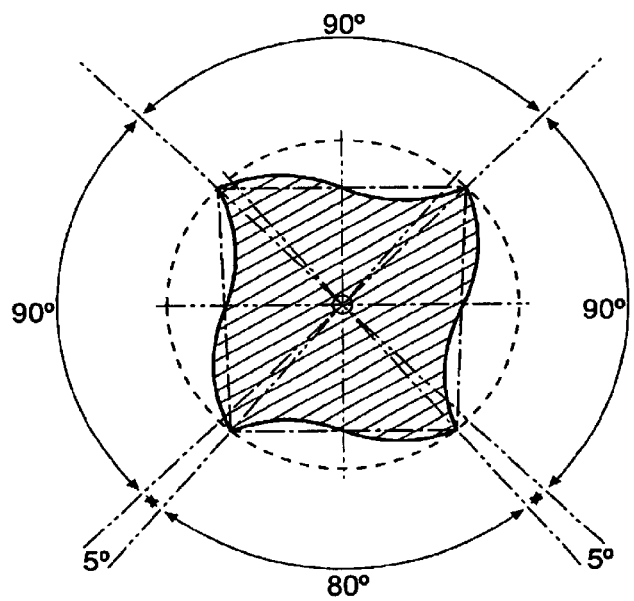
FIG._17D
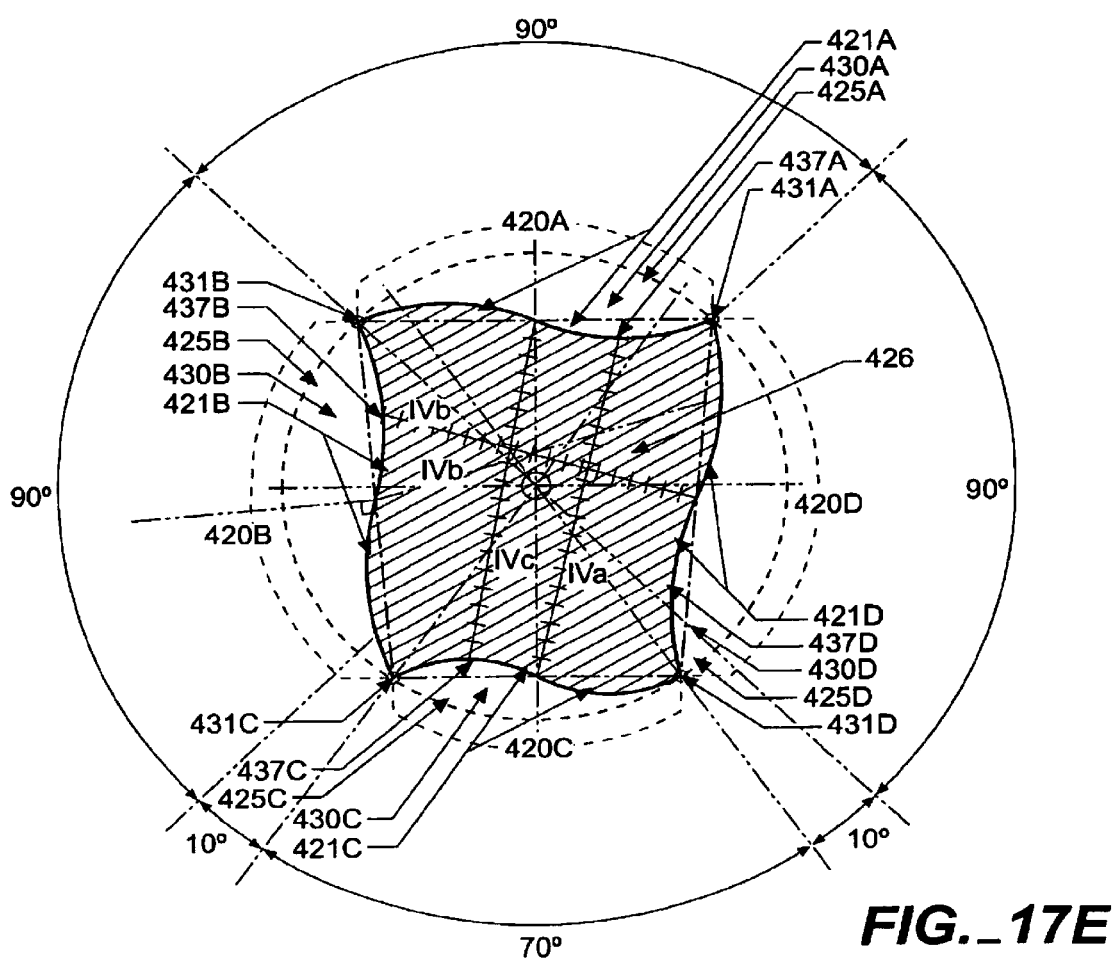
FIG._17E

CRITICAL PATH ENDODONTIC INSTRUMENTS FOR PREPARING ENDODONTIC CAVITY SPACES

This application claims the benefit of U.S. Provisional Application Ser. No. 60/467,472, filed May 1, 2003, Ser. No. 60/477,688, filed Jun. 10, 2003, and is a continuation-in-part and claims the benefit of priority under 35 U.S.C. Section 120 of U.S. application Ser. No. 10/764,337, filed on Jan. 22, 2004, pending, each of which is hereby incorporated by reference in their entireties.

BACKGROUND

The present invention relates to endodontic instruments.

Endodontic instruments can be used for cleaning and enlarging the endodontic cavity space ("ECS"), also known as the root canal system of a human tooth. FIG. 1A shows an example of an unprepared root canal 102 of a tooth 104. As can be seen, the unprepared root canal 102 is usually a narrow channel that runs through the central portion of the root of the tooth. Cleaning and enlargement of the ECS can be necessitated by the death or necrosis of the dental pulp, which is the tissue that occupies that space in a healthy tooth. This tissue can degenerate for a multitude of reasons, which include tooth decay, deep dental restorations, complete and incomplete dental fractures, traumatic injuries or spontaneous necrosis due to the calcification and ischemia of the tissue, which usually accompanies the ageing process. Similar to a necrotic or gangrenous appendix, the complete removal of this tissue is paramount, if not urgent, because of the subsequent development of infections or dental abscesses, septicemia, and even death.

The root canal system of a human tooth is often narrow, curved and calcified, and can be extremely difficult to negotiate or clean. Indeed, the conventional endodontic or root canal instruments currently available are frequently inadequate in the complete removal of the pulp and the efficient enlargement of the ECS. Furthermore, they are usually predisposed to breakage, causing further destruction to the tooth. Broken instruments are usually difficult, if not impossible to remove, often necessitating the removal of the tooth. Injury to the tooth, which occurs as the result of a frank perforation or alteration of the natural anatomy of the ECS, can also lead to failure of the root canal and tooth loss.

A root canal procedure itself can be better appreciated by referring to FIGS. 1A and 1B. The unprepared root canal 102 of the tooth 104 usually begins as a narrow and relatively parallel channel. The portal of entry or the orifice 106 and the portal of exit or foramen 108 are relatively equal in diameter. To accommodate complete cleaning and filling of the canal and to prevent further infection, the canal must usually be prepared. The endodontic cavity preparation ("ECP") generally includes progressively enlarging the orifice and the body of the canal, while leaving the foramen relatively small. The result is usually a continuous cone-shaped preparation, for example, the space 109.

In general, endodontic instruments are used to prepare the endodontic cavity space as described above. Endodontic instruments can include hand instruments and engine driven instruments. The latter can but need not be a rotary instrument. Combinations of both conventional hand and engine-driven rotary instruments are usually required to perform an ECP successfully and safely.

FIGS. 2A and 2B show a conventional endodontic instrument 200. The endodontic instrument shown includes a shaft 202 that includes a tip 204 and a shank 206. The endodontic instrument 200 also includes grooves 208 and 210 that spiral around the shaft 202. The grooves are referred to in the instant specification as flutes.

FIG. 2B shows a cross section 212 (i.e., cross section A—A) of the endodontic instrument. The cross section 208 shows cross sections 214 and 216 of flutes 208 and 210, respectively. As can be seen from FIGS. 2A and 2B, the flutes 208 and 210 are generally the spacing on both sides of a helical structure 218 (or helix) that spirals around the shaft 202. The bottom portion of a flute—seen as a line or curve (e.g., curve 220 indicated in bold)—is referred to in the instant specification as a spline (indicated by line in bold). The portion of a spline that comes into contact with a surface being cut during cutting will be referred to in the instant specification as a radial land. Item 222 of FIG. 2B is an example of a radial land.

A flute of an endodoritic instrument usually includes a sharpened edge configured for cutting. Edge 224 of FIG. 2A is an example of such a cutting edge. Edge 224 can be seen as a point 226 in FIG. 2B. Generally, an instrument having right-handed cutting edges is one that will cut or remove material when rotated clockwise, as viewed from shank to tip. In this specification, a direction of rotation will be specified as viewed from the shank to the tip of the instrument. The cut direction of rotation for a right handed endodontic instrument is clockwise. An instrument having left-handed cutting edges is one that will cut or remove material when rotated counter-clockwise. The cut direction of rotation, in this case, is counter-clockwise.

An endodontic instrument includes a working portion, which is the portion that can cut or remove material. The working portion is typically the portion along the shaft that is between the tip of the instrument and the shank end of the flutes. Portion 228 is the working portion for the endodontic instrument shown in FIG. 2A. The working portion is also referred to in this specification as the cutting portion, and the working length as the cutting or working length.

Hand instruments are typically manufactured from metal wire blanks of varying sizes. The metallurgical properties of these wires, in general, have been engineered to produce a wide range of physical properties. These wires are usually then twisted or cut to produce specific shapes and styles. Examples of hand instruments include K-type, H-type, and R-type hand instruments. FIG. 2C show a barbed broach 230, which is one example of an R-type instrument. FIG. 2D shows a cross section 232 (i.e., cross section A—A) of the barbed broach 230. The barbed broach is manufactured from soft iron wire that is tapered and notched to form barbs or rasps along its surface. These instruments are generally used in the gross removal of pulp tissue or debris from the root canal system. Another R-type file is a rat-tail file.

K-type instruments in current usage include reamers and K-files. FIG. 2E shows an example of a K-file 234. FIG. 2F shows a cross section 236 (i.e., cross section A—A) of the K-file 234. K files are generally available in carbon steel, stainless steel, and more recently, an alloy of nickel-titanium. To fabricate a K-type instrument, a round wire of varying diameters is usually grounded into three or four-sided pyramidal blanks and then rotated or twisted into the appropriate shapes. These shapes are specified and controlled by the American National Standards Institute ("ANSI") and the International Standards Organization ("ISO"). The manufacturing processes for reamers and files are similar; except however, files usually have a greater number of flutes per unit length than reamers. Reamers are used in a rotational direction only, whereas files can be used in a rotational or push-pull fashion. Files made from three-sided or triangular blanks have smaller cross sectional areas than files made from four-sided blanks. Thus, these instruments are usually more flexible and less likely to fracture. They also can display larger clearance angles and are more efficient during debridement. Triangular files, therefore, are generally considered more desirable for hand instrumentation.

FIG. 2G shows an example of an H-type file 238. FIG. 2H shows a cross section 240 (i.e., cross section A—A) of the H-type file 238. H-type files are usually manufactured by grinding flutes into tapered round metal blanks to form a series of intersecting cones. H-type files can usually cut only in the pull direction (i.e., a pull stroke). Primarily because they have positive cutting angles, H-type files can be extremely efficient cutting instruments.

Hand instruments are usually manufactured according to guidelines of the ANSI and the ISO, which specified that a working portion of an instrument be 16 mm in length. ANSI and ISO further specified that a first diameter or $D_1$ of the instrument, be 1 mm from the tip or $D_0$. Other ANSI and ISO specifications require that: instruments have a standard taper of 0.02 mm per mm along the working portion 216; the tip maintain a pyramidal shape no greater than 75° in linear cross section; and hand instruments (e.g., the ones shown in FIGS. 2A–2H) be available in 21, 25, and 31 mm lengths.

In addition to the hand instruments described above, there are rotary instruments that are usually motor driven. FIG. 3A shows an example rotary instrument 300 that is referred to as a G-type reamer or drill. FIG. 3B shows a cross section 301 (i.e., cross section A—A) of the G-type instrument. G-type drills are usually available in carbon or stainless steel. As is typical, the G-type drill 300 shown includes a short flame-shaped head 302 attached to a long shank 303. The core or web shown in FIG. 3B shows the cross sections 304, 305, and 306 of three flutes. The flutes, in this instance, have U-shaped splines. The instrument 300 includes cutting edges that have negative rake-angles. In general, a rake angle is the angle between the leading edge of a cutting tool and a perpendicular to the surface being cut. Rake angle is further described below. The flame-shaped head 302 includes a non-cutting surface to prevent perforation. The instrument 300 is usually used as a side-cutting instrument only. The instrument 300 is relatively rigid and, therefore, cannot usually be used in a curved space, for example, the ECS.

G-type drills are available in 14, 18 and 25 mm lengths as measured from tip to shank, which is where the drill can be inserted into a standard slow-speed hand piece via a latch grip 307. G-type drills are available in varying diameters of 0.30 mm to 1.5 mm and from sizes 1 through 6.

SUMMARY

The present invention provides methods and apparatus for providing a set of critical path endodontic instruments for preparing an endodontic cavity space.

In general, in one aspect, the invention provides a set of endodontic instruments for preparing an endodontic cavity space. The set includes a first endodontic instrument, a second endodontic instrument, and a third endodontic instrument. Each endodontic instrument includes a working portion that has a cone-like shape. Each working portion has an effective contact area defined by the exposed surface area of the working portion's respective cone-like shape. The difference between the effective contact areas of the first endodontic instrument and second endodontic instrument is substantially the same as the difference between the effective contact areas of the second endodontic instrument and third endodontic instrument.

In general, in another aspect, the invention provides an endodontic instrument for preparing an endodontic cavity space. The endodontic instrument includes a body that is configured to rotate about axis of rotation. The body has a center of mass that is off the axis of rotation, wherein the body is made of NiTi, and wherein the body is operable to swagger when rotated about the axis of rotation.

In general, in another aspect, the invention provides a set of endodontic instruments for preparing an endodontic cavity space. The set includes a first endodontic instrument, a second endodontic instrument, and a third endodontic instrument. Each endodontic instrument has a longitudinal axis. Each endodontic instrument has a cross sectional area at a predetermined point on its longitudinal axis. The predetermined point is substantially the same for the endodontic instruments of the set. The difference between the cross sectional areas of the first and second endodontic instruments is substantially the same as the difference between the cross sectional areas of the second and third endodontic instruments.

The invention can be implemented to realize one or more of the following advantages. The set of endodontic instruments configured as described in this specification reduces the chance of failure by equally or substantially equally allotting the amounts of dental material that is to be removed to prepare an endodontic cavity space among the instruments of the set. An endodontic instrument configured as described in this specification can swagger, as will be explained below, which allows one to prepare and clean the outer and the inner wall of the endodontic cavity space. Furthermore, the endodontic instrument has improved flexibility to allow the instrument to negotiate the tortuous, complex bends of a root canal. The instrument has improved cutting ability to allow the instrument to clean and enlarge the root canal efficiently. The endodontic instrument described, for example, includes features that allow the use of higher cutting torque and cutting speeds. The instrument has improved carriage capacity to haul debris to the coronal aspect of the tooth efficiently. The instrument has improved restoring force or resistance to bending to maintain the integrity of the instrument. The instrument has significant improved resistance to premature fatigue or breakage. The instrument has improved escapement and resistance to binding in the canal.

The details of one or more implementations of the invention are set forth in the accompanying drawings and the description below. Other features and advantages of the invention will become apparent from the description and the drawings.

BRIEF DESCRIPTION OF THE DRAWINGS

FIGS. 1A and 1B illustrate a root canal procedure.

FIGS. 2A–2H show examples of endodontic instruments.

FIGS. 3A and 3B show an example of a rotary-type endodontic instrument.

FIG. 4 shows an endodontic instrument having reversed helices.

FIG. 5 shows another endodontic instrument having reversed helices.

FIGS. 6A and 6B show other endodontic instruments having a reversed helices.

FIGS. 7A–7D show an endodontic instrument having cross cuts on its helices.

FIGS. 8A and 8B show an endodontic instrument having S-splines, positive cutting angles, and none or reduced radial lands.

FIGS. 9A–9H show an endodontic instrument having rolled edges and tapering.

FIGS. 10A–10C illustrate the notion of the critical set of endodontic instruments.

FIGS. 11A–11D illustrate the contact area of an endodontic instrument.

FIG. 12 illustrate the working portion of a critical path set of endodontic instruments.

FIGS. 13A–13E show one implementation of an endodontic instrument.

FIGS. 14A–14D show an endodontic instrument that includes a cutting tip.

FIGS. 15A–15D show another implementation of an endodontic instrument.

FIGS. 16A–16E show another implementation of an endodontic instrument.

FIGS. 17A–17E show another implementation of an endodontic instrument.

Like reference numbers and designations in the various drawings indicate like elements.

DETAILED DESCRIPTION

Reversed Helix

Conventional endodontic instruments have right-handed cutting edges and right-handed helices. A flute that forms a right handed helix spirals around the shaft, in a shank-to-tip longitudinal direction and, furthermore, in a clockwise direction of rotation (as viewed from shank to tip). This configuration is similar to the treads of a screw. Conventional endodontic instruments having this screw-like configuration are prone to binding. Furthermore, the radial lands and negative cutting angles typical of convention endodontic instruments predisposed the instruments to premature fatigue and breakage.

An endodontic instrument in accordance with the invention can include a reversed helix. A reversed helix spirals around the shaft of an instrument, in an shank-to-tip longitudinal direction and, furthermore, in a direction of rotation opposite to the cut direction of rotation. If, for example, the endodontic instrument has a clockwise cut direction of rotation, its helices would spiral in a counter-clockwise direction of rotation (along a longitudinal axis of the shaft in a shank-to-tip direction and as viewed from shank to tip). In this case, the instrument includes right-handed cutting edges. That is, the cutting edge is on the leading edge side of the helices as the instrument is rotated in the cut direction of rotation.

FIG. 4 shows an example of the described endodontic instrument. The instrument shown includes a shaft 402, helices 404 and 406, shank end (or simply end) 408, tip end (or simply tip) 410. The helix 406, for example, includes cutting edge 412. Thus, the instrument cuts when it is rotated about its longitudinal axis 418 in a counter-clockwise direction (as seen from an end-to-tip perspective), and the cut direction is counter-clockwise (as indicated by arrow 414). The direction which helices 404 and 406 spiral around the shaft 402 is clockwise (along the shaft in an end-to-tip direction and as viewed from an end-to-tip perspective; as indicated by arrow 416).

If the endodontic instrument has a clockwise cut direction of rotation (as seen from an end-to-tip perspective), then its flutes can spiral in a counter-clockwise direction of rotation (along a longitudinal axis of the shaft in an end-to-tip direction; and as viewed from an end-to-tip perspective). FIG. 5 shows and example of the described endodontic instrument. The instrument shown includes a shaft 502, helices 504 and 506, shank end (or simply end) 508, tip end (or simply tip) 510. The helix 504, for example, includes cutting edge 512. Thus, the instrument cuts when it is rotated about its longitudinal axis 518 in a clockwise direction (as seen from an end-to-tip perspective), and the cut direction is clockwise (as indicated by arrow 514). The direction which flutes 504 and 506 spiral around the shaft 502 is counter-clockwise (along the shaft in an end-to-tip direction and as viewed from an end-to-tip perspective; as indicated by arrow 516).

An endodontic instrument having the reversed helix is generally not prone to binding and can haul debris from its tip to its end, thus removing the debris from the space being prepared. In one implementation, the endodontic instrument can be fabricated from Ni—Ti or a Ni—Ti alloy. Engine driven instruments, including rotary engine driven instruments, as well as hand instruments can include the described reversed helix configuration.

In the above examples, the endodontic instruments shown included only two flutes. Endodontic instruments having any number of flutes and any spline geometry can incorporate the described reversed helix configuration. FIGS. 6A and 6B show implementations of multiple flute endodontic instruments having the reversed helix configuration.

Helices Having Cross Cuts

An endodontic instrument in accordance with the invention can include helices that include one or more cross cuts. The cross cuts of a helix can but need not be at right angles to the helix. In general, the cross cuts can have a geometry and depth so as to increase the flexibility of the endodontic instrument and allow the instrument to bend more easily. FIG. 7A shows an instrument 702 that includes helices having cross cuts. FIG. 7B shows a cross section 704 (i.e., cross section B—B) of the instrument 702. FIG. 7C shows the different example geometries which a cross cut can have. The cross cuts can include cutting edges, for example, cutting edge 706, which consequently provide a more efficient cutting device. FIG. 7D shows a cross section 708 (i.e., cross section A—A) of the instrument 702.

Web Designs Having S-shaped Splines, Positive Cutting Angles, and None or Reduced Radial Lands FIG. 8A shows an instrument 802, which is one example an endodontic instrument having an S-shaped spline, positive cutting angles, and none or reduced radial lands. The instrument 802 includes four helices 804, 806, 808, and 810 and four flutes 812, 814, 816, and 818. FIG. 8B shows a cross section 820 (i.e., cross section A—A) of the instrument 802. The web design shown exhibits a quadrilateral-like shape. FIG. 8B shows cross sections 822, 824, 826, and 828 of the flutes. The splines are S-shaped, which provides mass that can buttress the cutting edges of the instrument.

The cutting edges (shown as four arcs delimited by points 830, 832, 834, and 836) can have reduced positive cutting angles, which makes the cutting edges less prone to breakage than cuttings edge with large cutting angles. In the instant specification, a cutting angle of a cutting edge that is formed by a flute can be defined as the angle between (i) a tangent of the spline of the flute at the cutting edge and (ii) a ray extending radially outward from the center of cross section of the instrument. For example, the cutting edge at point 836 that is formed by flute 822 exhibits a cutting angle θ₁ defined by tangent 840 and ray 842. Tangent 840 can be mathematically represented as a one-sided derivative, taken at point 836, of a function that represents the spline 844. Alternatively, there are other ways of defining cutting angle. For example, the cutting angle can be defined as the angle θ₂ between the described tangent 840 and a tangent 846 of a circumference 848 of the instrument at point 836. Under the alternative definition, the cutting angle θ₂ is said to be neutral or zero when the angle is ninety degrees, positive when greater than ninety degrees, and negative when less than ninety degrees.

An S-shaped spline also removes the radial land usually present in conventional endodontic instruments. The crossed hatched area 850 represents a hypothetical radial land. As can be seen, the radial land, if present, would rub against a surface being cut and create unnecessary drag along the working surface of the instrument and render it inefficient and predisposed to breakage.

The described endodontic instrument can be fabricated from a preformed cylindrical metal blanks of nickel titanium. Alternatively, the instrument can be fabricated from others blanks and other materials.

The shank end of the above described instrument can include a latch-type attachment suitable for coupling, usually detachably, to a motor driven chuck. The latch-type attachment can also be suitable for coupling to a handle if the instrument is to be used manually. The tip of the instrument can be smooth while maintaining the conicity, taper, and transverse cross-sectional shape of the instrument.

The following describes an implementation. The tip of the implementation ends in a pyramidal or parabolic shape and is at least 0.05 mm in diameter and 1–3 mm in length. The cutting length (not including the tip) of the implementation is 8–16 mm in length. In general, the cutting length should be at least 2 mm in length. The cutting edges of the implementation is created by including one to six flutes. Alternatively, the implementation can include additional flutes. The flutes usually begin at a first position near the shank end of the instrument and ends at a second position near the tip end of the instrument. The first position is referred to as a maximum flute diameter (or MxFD) and the second position is referred to as a minimum flute diameter (or MnFD). The flutes are concave and are substantially the same as each other. The flutes have a shape and depth that remains constant along the length of the shaft. Alternatively, the shape and/or depth can vary along the length of the shaft. These flutes are spaced along the circumference of the cutting surface. The spacing can be of uniform intervals or irregular intervals. That is, the helix formation or spirals that progress from the shank end to the tip of the instrument can be spaced at regular intervals or increasingly narrower intervals. In the latter case, a greater number of spirals can be included per unit length along the longitudinal axis of the implementation. Each flute forms a neutral or slightly positive cutting angle. The flutes spiral around the shaft of the instrument, completing 360° of rotation for a minimum of 1 mm, and a maximum of 6 mm of axial length of the cutting surface.

Variable Working Surfaces with Flute Modifications and/or Attenuated Cutting Edges The working surfaces or leading edges of conventional endodontic instruments have been manufactured with active or sharp cutting edges along the entire length of the working surface. This configuration can predispose the instrument to great amounts of torque leading to premature fatigue and breakage. One can mitigate the problem by varying the taper and the length of the working surface. As the instrument increased in diameter, the length of the working surface, or the number of cutting flutes (i.e., the number of flutes that form cutting edges) per unit length along the longitudinal axis of the instrument, can be reduced. Although, this configuration does mitigate the amount of torque that the instrument engenders as the size of the instrument increases, eliminating flutes also eliminates the ability of the instrument to continue to haul debris coronally. As a result, the instrument can become easily clogged creating unnecessary drag on the instrument.

An endodontic instrument in accordance with the invention retains the flutes along the entire length of the working surface to maintain hauling action. The leading edge or the working surface, however, is modified such that only a portion of the working surface cuts. This modification is brought about by blunting or rolling the edge of flutes both at the tip and shank ends of the instrument, leaving the central portion of the cutting surface active. Rolling edges will prevent the instrument from over-enlarging or tearing the foramen of the ECS distally and mitigate drag and pre-mature fatigue proximally. FIGS. 9A–9D show an example instrument that includes a reduced working portion. FIG. 9A shows the instrument 902. FIG. 9B shows the working portion 904 of the instrument 902. FIG. 9C shows a non-cutting tip portion 906 of the instrument 902. FIG. 9D shows a non-cutting shank-end portion 908 of the instrument 902. FIGS. 9E–9H show an implementation in which the instrument 902 tapers from shank to tip.

Endodontic instruments can be provided in sets. A set usually includes instruments of different diameters. In preparing an ECS, an endodontist usually begins the preparation process using the instrument having the smallest diameter. As the ECS is enlarged, the endodontist usually switches to instruments of progressively larger diameters. The rolled edges feature described above can vary from one instrument to another in a set of instruments, with the active surface diminishing in length progressively as the diameter of the instrument increased. This feature would allow the instrument to continue to haul debris coronally, but mitigate the torque that the instrument is subject to when cutting.

Critical Path Set of Endodontic Instruments

A set of endodontic instruments, the instruments of which can have the same length but different diameters, can be provided for use in seriatim to enlarge progressively the ECS 102 of a tooth (FIG. 1A) and create the continuous cone-shaped space 109 (previously shown in FIG. 1B and also shown in FIG. 10A). In particular, the instrument with the smallest diameter is first used to enlarge the ECS 102 to a certain extent. Then, the instrument with the next largest diameter is used to further enlarge the ECS. This process continues until the instrument having the largest diameter is used to complete the creation of the space 109. Progressively enlarging the ECS 102 as described above can usually subject the tooth and the endodontic instruments to stress that is significantly less than the stress that would be exerted if only one instrument were used to created the space 109.

The stress level to which an endodontic instrument is subject can be related to the amount of material the instrument removes. In view of the forgoing, the number of endodontic instruments provided in the set as well as their sizing can be determined so that each instrument of the set is subject to a similar or the same level of stress during its use to remove its apportioned amount of dental material. The determination can be based on a critical set model that will be explain in the following paragraphs.

The indicated portion of the space 109 (FIG. 10A), which generally starts at the point in the ECS (referred to below as the curve-start point) where a straight-line preparation is no longer practical or possible and ends at the foramen of the ECS, can be modeled as the geometric object 1002 shown in FIG. 10B. The object 1002 represents the curved portion of an ideally prepared ECS.

The object 1002 can be incremented along its length, which is typically 12 millimeters, into 12 one-millimeter sections. As can be seen, the transverse cross-sections that so increment the space 109 are circles that are denoted as 50, 51, . . . , 62, where the cross section 50 is at the tip and cross section 62 is at the butt of the space 109.

Note that the shaft (not shown) of each endodontic instrument of the set can be similarly incremented by transverse cross-sections denoted as $D_1, D_2, \ldots, D_{12}$, each of which can correspond to a respective cross section of the space 109. $D_6$, for example, corresponds to cross section 56.

The cross section 56 represents the portion of the ECS that has the greatest curvature, usually referred to as the fulcrum. The fulcrum usually occurs at or near the midpoint between the foramen and the above described curve point of the ECS and, furthermore, is generally the point where endodontic instruments are most vulnerable to failure, including, for example, catastrophic breakage.

The set of endodontic instruments can be configured to reduce the probability of failure at or near the D6 cross sections of their shafts. In particular, the set can be configured so that the total amount of dental material to be removed at and around cross section 56 is evenly distributed among the instruments of the set. A set of instruments so configured will be referred to as the critical path set.

FIG. 10C shows the cross section 56, which includes seven circles, i.e., circles 1003–1009. The circles can define six annuli of equal area. The circles 1003–1009 have, respectively, diameters $d_0$–$d_6$ and radii $r_0$–$r_6$. Note that circle 1003 and 1009 correspond, respectively, to the perimeters of cross section 50 and cross section 56. Each annulus can be defined by its outer and inner circle and, furthermore, can represent the amount of dental material that an instrument is used to remove. The instruments can be sized so that their cross sections at $D_6$ correspond to the circles 1004–1009. That is, the nth instrument is to have a $D_6$ cross section diameter of $d_n$. The first instrument, for example, is to have a $D_6$ cross section diameter of $d_1$.

As can be seen from FIG. 10C, an annulus has an outer circle and inner circle. The area of an annulus can be calculated by taking the difference between the area of the outer circle and the area of the inner circle. Given that ECS is to be enlarged sequentially from 0.20 to 0.70 mm at $D_6$ (and 0.20 to 1.2 mm at $D_{12}$), the area of the annulus defined by circles 1003 and 1009, which as discussed can represent the total amount of material to be removed at or around D6, can be calculated as:

$$A_{outer\ circle} - A_{inner\ circle} = \pi(0.35)^2 - \pi(0.1)^2$$

$$A \text{ of annulus at } D_6 = \pi(0.1225) - \pi(0.01)$$

$$A \text{ of annulus at } D_6 = \pi(0.1125)$$

For a set of six instruments, the amount of material allotted to each instrument to remove can be represented by diving the above calculated total area by six. Each instrument would then have an increase in cross sectional area at $D_6$ by one-sixth the area calculated above (i.e., the area of the annulus defined by circles 1003 and 1009 at $D_6$), which is calculated as:

$$(A \text{ of annulus at } D_6)/6 = [\pi(.1125)]/6$$
$$= \pi 0.01875$$

In general, a formula to determine the D6 radius of an nth instrument can be defined as:

$$\pi r_n^2 = \pi(r_{n-1})^2 + \pi 0.01875$$

$$r_n^2 = (r_{n-1})^2 + 0.01875$$

$$r_n = [(r_{n-1})^2 + 0.01875]^{1/2}$$

where n represents the sequential position of the instrument in the sequence of instruments in the set, the sequence being based on size. The first instrument in the set, for example, is usually the smallest sized instrument and is the one of the set that is first used to prepare the ECS. Thus, n is an integer that is at least 1. Additionally, $r_n$ is the radius of the $D_6$ cross section of the nth instrument, except for $r_0$, which is the radius of the circle 1003 (i.e., the diameter of the unprepared ECS at D6) shown in FIG. 10C. Alternatively, the formula can be defined as:

$$\pi r_n^2 = \pi(r_0)^2 + n(\pi 0.01875)$$

$$r_n^2 = (r_0)^2 + n(0.01875)$$

$$r_n = [(r_0)^2 + n(0.01875)]^{1/2}$$

Furthermore, the radius of the $D_6$ cross section of smallest instrument of the set, i.e., instrument No. 1, which corresponds to the radius of the ECS cross section resulting after the first instrument is used to prepare the ECS is:

$$r_1^2 = ro^2 + 0.01875$$

$$r_1^2 = (0.1)^2 + 0.01875$$

$$r_1^2 = 0.010 + 0.01875$$

$$r_1^2 = 0.0388$$

$$r_1 = 0.1696$$

Thus, the diameter of the $D_6$ cross section of the first instrument is:

$$d_1 = 0.339 \text{ mm}$$

Using either formula [1] or formula [2], the values for $d_2$, $d_3$, $d_4$, $d_5$, and $d_6$ can be derived. Table 1 shows the derived cross-sectional diameters, $d_1$, $d_2$, $d_3$, $d_4$, $d_5$, and $d_6$, that occur at $D_0$, $D_6$, and $D_{12}$. The superscript percentages, e.g., those listed in row D6, each represents the percentage increase in cross-sectional area from the previous diameter or instrument. The average of these changes from $d_1$–$d_6$ at $D_6$ is 24%. The average of the changes from $d_1$–$d_5$ at $D_6$ is 29%.

TABLE 1

|     | $d_0$ | $d_1$ | $d_2$ | $d_3$ | $d_4$ | $d_5$ | $d_6$ |
| --- | --- | --- | --- | --- | --- | --- | --- |
| D0  | 0.20 | 0.20 | 0.20 | 0.20 | 0.20 | 0.20 | 0.20 |
| D6  | 0.20 | $0.339^{70\%}$ | $0.436^{28\%}$ | $0.515^{15\%}$ | $0.583^{13\%}$ | $0.644^{10\%}$ | $0.7000^{8\%}$ |
| D12 | 0.20 | 0.522 | 0.712 | 0.86 | 0.986 | 1.098 | 1.2 |

Table 2 show the cross section diameters of a set of instruments that is similar to the critical set. The average increase in diameter is 29%, which, notably, is achieved by logarithmic progression and not linear progression of conventional set, as is the case in conventional sets of instruments.

TABLE 2

|     | 15/05 | 20/06 | 24/07 | 27/08 | 29/09 | 30/10 |
| --- | --- | --- | --- | --- | --- | --- |
| D1  | 15 | 20 | 24 | 27 | 29 | 30 |
| D2  | 20 | 26 | 31 | 35 | 38 | 40 |
| D3  | 25 | 32 | 38 | 43 | 47 | 50 |
| D4  | 30 | 38 | 45 | 51 | 56 | 60 |
| D5  | 35 | 44 | 52 | 59 | 65 | 70 |
| D6  | $40^{100\%}$ | $50^{25\%}$ | $59^{18\%}$ | $67^{13\%}$ | $74^{10\%}$ | $80^{8\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |
| D7  | 45 | 56 | 66 | 75 | 81 | 90 |
| D8  | 50 | 62 | 73 | 83 | 90 | 100 |
| D9  | 55 | 68 | 80 | 91 | 99 | 110 |
| D10 | 60 | 74 | 87 | 99 | 108 | 120 |
| D11 | 65 | 80 | 94 | 107 | 117 | 130 |
| D12 | 70 | 86 | 101 | 115 | 126 | 140 |

Table 3 shows the cross section diameters of another set of instruments that is similar to the critical set. The percent change in the $D_6$ cross section diameter of this set is also 29%. Note however, that there is a substantial increase in the diameter of the instruments from $d_5$ to $d_6$, which can still be considered safe, because the rigidity of this instrument prevents any meaningful flexure eliminating fatigue and breakage.

TABLE 3

|     | 15/04 | 20/05 | 24/06 | 27/07 | 30/08 | 35/10 |
| --- | --- | --- | --- | --- | --- | --- |
| D1  | 15 | 20 | 24 | 27 | 30 | 35 |
| D2  | 19 | 25 | 30 | 34 | 38 | 45 |
| D3  | 23 | 30 | 36 | 41 | 46 | 55 |
| D4  | 27 | 35 | 42 | 48 | 54 | 65 |
| D5  | 31 | 40 | 48 | 55 | 62 | 75 |
| D6  | $35^{75\%}$ | $45^{28\%}$ | $54^{20\%}$ | $62^{15\%}$ | $70^{13\%}$ | $85^{21\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |

Table 4 shows the cross section diameters of yet another set of instruments that is similar to the critical set. These instruments corresponds very closely to a critical set at $D_6$. The average increase in the $D_6$ cross section diameter from the first to the fifth instrument is 29%, which is identical to the critical set. The instrument with the smallest diameter, the 15/04 can also be discounted or set aside from a critical set, because it is extremely flexible and intrinsically safe.

Optionally, where a set includes one or more instruments that have cross sectional diameters that vary along the shaft, as is the case for the instruments represented in the tables included in this specification, one can roll the cuttings edges of portions of an instrument that has the same diameter as another instrument of the set. Doing so can reduce the resistance to which the instrument is subject and make the instrument even less predisposed to failure. In the tables, shaded cells indicate that the portions listed in the cells can have rolled edges.

TABLE 4

|     | 15/04 | 20/05 | 23/06 | 25/07 | 27/08 | 30/10 |
| --- | --- | --- | --- | --- | --- | --- |
| D1  | 15 | 20 | 23 | 25 | 27 | 30 |
| D2  | 19 | 25 | 29 | 32 | 35 | 40 |
| D3  | 23 | 30 | 35 | 39 | 43 | 50 |
| D4  | 27 | 35 | 41 | 46 | 51 | 60 |
| D5  | 31 | 40 | 47 | 53 | 59 | 70 |
| D6  | $35^{75\%}$ | $45^{29\%}$ | $53^{18\%}$ | $60^{13\%}$ | $67^{12\%}$ | $80^{19\%}$ |
| D6 Critical | $.339^{70\%}$ | $.436^{28\%}$ | $.515^{15\%}$ | $.583^{13\%}$ | $.644^{10\%}$ | $.7000^{8\%}$ |
| D7  | 39 | 50 | 59 | 67 | 75 | 90 |
| D8  | 43 | 55 | 66 | 74 | 83 | 100 |
| D9  | 47 | 60 | 72 | 81 | 91 | 110 |
| D10 | 51 | 65 | 78 | 88 | 99 | 120 |
| D11 | 55 | 70 | 84 | 95 | 107 | 130 |
| D12 | 59 | 75 | 90 | 102 | 115 | 140 |

Table 5 shows the cross section diameters of yet another set of instruments that is similar to the critical set. These instruments deviate slightly from the critical set; however, it mimics tips sizes and tapes that are familiar to most practitioners.

TABLE 5

|     | 15/04 | 20/05 | 25/06 | 30/07 | 35/08 | 40/10 |
| --- | --- | --- | --- | --- | --- | --- |
| D1  | 15 | 20 | 25 | 34 | 36 | 40 |
| D2  | 19 | 25 | 31 | 41 | 44 | 50 |
| D3  | 23 | 30 | 37 | 48 | 52 | 60 |
| D4  | 27 | 35 | 43 | 55 | 60 | 70 |
| D5  | 31 | 40 | 49 | 62 | 68 | 80 |
| D6  | $35^{75\%}$ | $45^{28\%}$ | $55^{22\%}$ | $69^{25\%}$ | $76^{11\%}$ | $90^{18\%}$ |
| D6 Critical Set | $.339^{70\%}$ | $.436^{28\%}$ | $.515^{15\%}$ | $.583^{13\%}$ | $.644^{10\%}$ | $.7000^{8\%}$ |

These calculations and the instrument sets that have been proposed are again, functions of the formula for the area of a circle. Similar calculations can be also be made using formulas for circumference of a circle or the surface area of a frustum. Further, calculations can also be made using the average of the surface areas of all the intersecting diameters of the critical path, their circumferences, the surface areas of the frustums or portions or combinations thereof.

One alternative, for example, can be implemented such that the above-described equal distribution of dental material to be removed can be calculated not only for the $D_6$ cross section, but for any combination of $D_1$–$D_6$ cross sections, or even for any cross section or every cross sections along the axis of the shaft.

The above described differences in D6 cross-section areas of instruments, for example, the difference in the $D_6$ cross-section areas of the first and second instruments and the difference in the $D_6$ cross-section areas of the second and third instruments, need not be exactly equal. The differences in areas can be substantially equal, for example, one difference being no more than twice the other difference.

The cross sections used in the above described model need not be $D_6$ cross sections but can be cross sections substantially the same as the $D_6$ cross section. Cross sections within 5 millimeters of the $D_6$ cross section, for example, can be used in the model.

As an another alternative, a critical set can be defined based on a calculation of the effective contact area of each endodontic instrument in a set of endodontic instruments. The effective contact area is the exposed surface area of a cone-like shape, which, for an endodontic instrument, is defined as shown in FIGS. 11A and 11B. The example endodontic instrument 1102 shown includes a working portion 1104, which as discussed above, is the portion of the instrument that includes cutting edges, e.g., cutting edge 1106. The working portion includes cross sections, each defining a circle into which the corresponding cross section can be inscribed. The circle having the greatest diameter is usually defined by the largest cross section, which usually occurs at or near the proximal end of the working portion (i.e., the end that is closest to the shank and farthest away from the tip of the endodontic instrument). The circle having the smallest diameter is usually defined by the smallest cross section, which usually occurs at or near the distal end of the working portion (i.e., the end that is closest to the tip). In most cases, the described largest and smallest circles are the base 1108 and the top 1110, respectively, of a cone-like shape 1112. The base 1108 has a first diameter and the top 1110 has a second diameter that is usually smaller than the first diameter. The distance along the longitudinal axis 1114 of the endodontic instrument defines the height 1116 of the cone-like shape 1112. This cone-like shape 1112 has an exposed surface area called a frustrum, which excludes the surface area of the base 1108 and the top 1110. The exposed surface area can be mathematically defined, for example, by integrating the circles described along the height of the cone-like shape.

When a critical set is based on the described effective contact area (i.e., the described surface area of the cone-like shape), the endodontic instrument in a critical set of endodontic instruments can be sized such that the increase of the effective contact area from one endodontic to the next greater sized endodontic instrument is substantially the same. FIGS. 11C and 11D show six example cone-like shapes of an example critical set of endodontic instruments. The change in surface area between any adjacent shapes is substantially constant. In cases where an endodontic instrument includes a working portion that runs to the tip of the instrument, the cone-like shape is a cone.

Alternatively, a critical set can be defined differently from the ways described above. The criterion that should be satisfied is that each endodontic instrument in a set be subject to substantially the same level of torsional stress. Distributing the torsional stress as described reduces breakage.

Distribution of the torsional stress can be fined tuned by changing the working portion of an instrument, as was described above. Reducing the working portion of an instrument, for example, can reduce the level of torsional stress to which the instrument is subject during its use. FIG. 12 shows an implementation of a set of endodontic instruments where the working portion varies from instrument to instrument so that the instruments are subject to substantially the same level of stress during their use. (The dashed lines 1202 and 1204 delimit the working portions.)

A critical set can include more or less than six instruments. The number of instrument depends on the amount of dental material to be removed, with more instruments being needed to removed more dental material. The number of instruments, however, should not be so numerous as to impeded the ECS preparation by requiring the practitioner to frequently switch instruments.

Swagger

The phenomenon of "swagger" is viewed as a transverse mechanical wave, which can be modified, and is comparable to the transverse wave that is being produced along a stretched rope or string when it is oscillated. If one ties one end of a long rope to a stationary point, stretches the rope out horizontally, and then gives the end being held a back-and-forth transverse motion, called the excitation force, $F_e$, the result is a wave pulse that travels along the length of the rope. Observation shows that the pulse travels with a definite speed, maintaining its shape as it travels, and that the individual segments making up the rope move back and forth in a direction perpendicular to the rope's equilibrium position. In physics, this principle can be expressed mathematically by the formula $y=f(x, t)$. Here, the equilibrium position is along the x-axis (corresponding to the stretched rope), and the transverse displacement of any point away from this position (corresponding to the maximum displacement of the rope) is y. Thus, y is a function of both x (the undisplaced position of the point) and time t. This is called the wave function.

At any time t, if one takes a picture of the instantaneous shape of the rope, one finds that y varies sinusoidally with x.

This same system can function in another dimension, where an excitation force is applied along both the y- and the z-axes. Here, at any time t, if one takes a picture of the instantaneous shape of the rope, one finds that y and z vary sinusoidally with x simultaneously. Using the stretched rope as an example, the rope is now observed to produce a spiral or helical wave. In a similar context, if one applies a lateral force, $F_l$, somewhere along the x-axis, while the rope is oscillating sinusoidally in the y dimension, the same phenomenon is observed, that is, the portion of the rope adjacent to, and distal to the lateral force, will also spiral.

In preparing an endodontic cavity space, which is curved along the critical path with a flexible rotary instrument, a similar system can be configured. The instrument is bound in a somewhat fixed position at one end, by the elbow or greater curvature of the canal, and at the other end by the head of the hand piece. Observation of an endodontic instrument with a symmetric transverse cross-section, rotating in an endodontic cavity space appears to have little, if any, deviation from the x-axis. An instrument with an asymmetrical cross-section, acts like a rope with an excitation force or forces applied along the x-axis, or one with an excitation force y and a lateral force applied somewhere along its length. The lateral force, in this instance, is the differential that is produced by relocating the center of mass of the instrument away from the x-axis.

Most of the mathematics for helical wave theory focuses on hydrodynamics, acoustics and electromagnetic fields. Fortunately, Newtonian physics provides a plethora of laws and principles, which can be applied to this phenomenon.

If one considers the relationship between torque $\lambda$ and angular acceleration a of a point mass m one can better understand the physical nature of swagger. A mass m moving in a circle of radius r acted on by a tangential force $F_t$ is shown in the figure below.

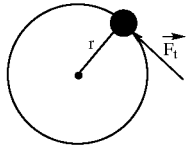

Using Newton's second law to relate $F_t$ to the tangential acceleration $a_t = ra$ where a is the angular acceleration:

$$F_t = ma_t = mra.$$

And the fact that the torque about the center of rotation due to $F_t$ is $\lambda = F_t \cdot r$, one arrives at:

$$\lambda = mr^2 a.$$

If one attempts to apply the above equations to an endodontic instrument, which is tapered from its proximal to its distal end, then each cross-sectional area or lamina along its length has a different mass. Thus, for a rotating rigid body, such as a tapered endodontic instrument made up of a collection of masses $m_1, m_2 \ldots m_i$, the total torque about the axis of rotation is:

$$\lambda = \Sigma \lambda_i = \Sigma (m_i r_i^2) a.$$

The angular acceleration of all the points in a rigid body are considered to be the same, thus the equation can be taken outside the summation. Thus, if a constant torque $\lambda i$, as is applied in a torque controlled dental hand piece, were applied to a fixed mass $m_i$, the acceleration of $m_i$ would increase or decrease exponentially as the radius r of $m_i$ changed.

Torque, like the waves along a stretched rope, must be defined about a particular set of axes. If one further considers the moment of inertia, I, of a rigid body with $m_i$, a measure of the amount of resistance the body has to changing its state of rotational motion is given. Thus, for a rotating rigid body, made up of a collection of masses $m_1, m_2 \ldots m_i$, the total inertia about the axis of rotation is expressed mathematically, $$I = \Sigma m_i r_i^2$$

The units of moment of inertia are kg m²

$$\lambda = Ia.$$

This is the rotational analogue of Newton's second law. The complete set of dynamical equations needed to describe the motion of a rigid body consists of the torque equation given above, plus Newton's Second Law applied to the center of mass or the centroid of the object:

$$F_{total} = ma_{cm}$$

Where, $a_{cm}$ is the acceleration of the center of mass.

The moment of inertia, like torque must also be defined about a particular set of axes. It is different for different choices of axes.

Extended objects can again be considered as a very large collection of much smaller masses glued together to which the definition of moment of inertia given above can be applied.

Like torque, the moment of inertia depends on how the mass is distributed about the axis. For a given total mass, the moment of inertia is greater if more mass is farther from the axis, than if the same mass is distributed closer to the axis.

The various masses, i.e., cross-sections or laminas, which are distributed along the transverse axis of an endodontic instrument are turning about that transverse axis. The tangential force and/or inertia of the center of mass of each section or lamina of the instrument taken at any point along the transverse axis varies. This varied tangential force or moment predisposes the instrument to oscillate, which in combination with the rotation of the instrument by the dental hand piece creates a helical envelope of motion. This helical envelope of motion now displaces the body of the instrument allowing it to cut intermittently at a given point along the transverse axis. In the case of a curved endodontic cavity space, the instrument will not bind against the outer wall, as does an instrument of symmetric cross-section, but cut both the inner and outer walls of the curve more evenly.

Returning to a planar lamina which extends across a region R in the plane, so that at each point (x, y) in R there is a variable mass density r(x, y), measured in units of mass per unit area, then the total mass of the lamina is given by the double integral:

$$m = \iint_R \rho(x, y) dA$$

The moment $M_y$ of the lamina with respect to the y-axis is then $\iint_R x \rho(x, y) dA$ and similarly $M_x = \iint_R y \rho(x, y) dA$. Further, the same formulas we used above allow us to find the center of mass (X, Y) of the lamina.

Thus, for a given cross-section or lamina, taken at any region R, the appropriate location of the center of mass of the asymmetric instrument can be pre-determined if the displacement of the body of the instrument from the axis of rotation to the outer wall of the endodontic cavity space has a radius r is measurable.

Although more complex, similar calculations can be made in 3D-space, using similar formulas. For instance, $M^{xy} = \iiint_S z \rho(x, y, z) dV$ is the moment of the solid S about the xy-plane, and the center of mass (X, Y, Z) of S satisfies the equations:

$$X = M_{yz}/m, \quad Y = M_{xz}/m, \quad Z = M_{xy}/m,$$

$m = \iiint_S \rho(x, y, z) dV$ being the total mass of S.

Implementations

FIGS. 13A–13E illustrate one implementation. The endodontic instrument 1110 includes three sides, is triangular in transverse cross-section, and can be utilized to remove tissue and/or dentin from an ECS. The instrument 1110 includes a shank 1111 and a working portion 1112, which is tapered in a shank-to-tip direction. The tip 1113 includes an active or cutting surface, which is confluent the working surface 1112 (for example, like the tip shown in FIGS. 14A–14D). Alternatively, the leading tip 1113 (of the instrument shown in FIGS. 13A–13E) can include a non-active or non-cutting surface, which is also confluent with the working surface 1112 (for example, like the tip shown in FIG. 9C). The MxFD 1117 is located near the shank end of the cutting surface and MnFD 1116 is located near the tip 1113. The shank 1111 above the working portion 1112 is essentially cylindrical and exhibits a slightly smaller diameter than the cutting surface at the MxFD. The instrument 110 includes rolled-edge portion 114, which is confluent with the working portion 1112. This rolled-edge modification is illustrated in FIGS. 9A–9D. A fitting 1115, which is suitable for an engine driven motor with a hand-piece and chuck, or a handle utilized for manual instrumentation, is attached to the shank 1111.

As shown in FIGS. 13A–13E, three continuous-helical flutes 1120A, 1120B and 1120C are substantially concave grooves which follow the circumference of the working surface 1112 spiraling toward the leading tip 1113 forming concentric circles. These flutes may be equidistant from each other or become increasingly tighter or more numerous as they approach the tip. The total number of flutes from MxFD to the MnFD should be no fewer than 16 but not greater than 24. Helical flutes 1120A, 1120B and 1120C each originate at the MxFD at separate locations that are equally spaced apart around the circumference of the shank 1111 or more specifically at 120° of separation. Each helical structure (i.e., the mass between the flutes) is continuous along the length of the cutting surface 1112 to the leading tip 1113.

With reference to FIG. 13E, it can be seen that flutes 1120A, 1120B and 1120C have S-shaped splines 1121A, 1121B and 1121C. The flutes 1120A, 1120B and 1120C form helical cutting edges 1125A, 1125B and 1125C at the periphery of the shank 1111. A transverse cross-section is shown of the cutting portion 1112. The helical flutes 1120A, 1120B and 1120C cooperate to form a web or core 1126, which is essentially triangular. Areas of radial clearance or cutouts created by the flutes 1121A, 1121B and 1121C outline the web or core. These areas of clearance are designated by numerals 1130A, 1130B and 1130C. In transverse cross-section of the shank 1111, splines 1121A, 1121B, and 1121C of cutting flutes 1120A, 1120B, and 1120C form teardrop-shaped clearance areas of variable depth. The cutting surfaces 1125A, 1125B, and 1125C, or the perimeter of the shank, and the splines of the inner walls 1121A, 1121B, and 1121C circumscribe clearance areas 1130A, 1130B, and 1130C.

With further reference to FIG. 13E, it can be seen that walls 1121A, 1121B, and 1121C intersect the periphery of the shank 1111 at points 1131A, 1131B, and 1131C. These intersections are equal distances apart or at 120° of separation forming a neutral cutting angle (90° angle to the tangent of the perimeter of shank 1111) or slightly positive cutting angle (greater than 90° to the tangent of the perimeter of the shank 1111). Lines drawn connecting point 1131A, 1131B, and 1131C form an equilateral triangle. As shown in FIG. 13D, points 1131A, 1131B, and 1131C intersect the periphery of the shank 1111 alternately at 110°, 125°, and 125° of separation. Lines drawn connecting the point 1131A, 1131B, and 1131C form an isosceles triangle. The outline of the triangle that is formed connecting point 1131A, 1131B, and 1131C can vary. The outline may also be a scalene triangle with unequal sides. The difference in the number of degrees of separation between the longest spline and the short spline is not less than 600 and not greater than 150°.

The splines 1121A, 1121B, and 1121C are S-shaped and are individually symmetrical. The bisector of each spline divides the spline equally into convex and a concave segments which form the S-shaped curve. The lines that bisect each spline can be drawn to the center of the core 1126 and are equal in length. Further, an alternate bisector a can be drawn from the center of each spline through the greatest concavity the adjacent spline and perpendicular to the lines, which form the equilateral triangle. The bisectors a for each spline 1121A, 1121B, and 1121C are equal.

The greatest depth of each spline can be defined by a segment of a. These depths can vary and, furthermore, be calculated as a percentage of the length of a. The greatest depths of splines 1121A, 1121C, and 1121B, indicated with demarcated line segments 1137A, 1137B, and 1137C, are 15%, 20%, and 25% of the length of a, respectively. The greatest convexities of splines 1121A, 1121B, and 1121C are mirror images of the greatest concavities of the same splines. The depth and height of each spline can vary; however, the cross sectional diameter of the core portion 1126 should generally not be narrower than approximately half or fifty percent of the cross sectional diameter of the shank of the instrument.

FIGS. 15A–15D illustrate another implementation, which is four sided or rectilinear in transverse cross-section and can be utilized to remove tissue and/or dentin from an ECS. The implementation shown includes a shank similar to the one described in FIGS. 13A–10E and a working portion 1212, which is tapered in a shank-to-tip direction. The tip 1213 can include a cutting surface, which is confluent the working surface 1212 (for example, like the tip shown in FIGS. 14A–14D). Alternatively, the leading tip 1213 (of the instrument shown in FIGS. 15A–15D) can include a non-cutting surface, which is confluent with the working surface 1212 (for example, like the tip shown in FIG. 9C). The MxFD 1217 is located near the shank end of the cutting surface and MnFD 1216 is located near the tip end of the cutting surface. The shank 1211 above the cutting surface 1212 is essentially cylindrical exhibiting a slightly smaller diameter than the cutting surface at the MxFD (also similar to the instrument described in FIGS. 13A–13E). The instrument can include a modified or rolled edge portion 1214, which can to be confluent with the cutting surface 1212. This rolled-edge feature is illustrated in FIGS. 9A–9D. A fitting, which is suitable for an engine driven motor with a hand-piece and chuck or a handle utilized for manual instrumentation, is attached to the shank at its most proximal end (also similar to the fitting described in FIGS. 13A–13E).

With further reference to FIGS. 15A–15D, four continuous helical flutes 1220A, 1220B, 1220C, and 1220D are substantially concave grooves which follow the circumference of the working surface 1212 spiraling toward the leading tip 1213 forming concentric circles, which may be equidistant from each other or becoming increasingly tighter or more numerous as they approach the tip 1213. The total number of flutes from MxFD to the MnFD should be no fewer than 16 but not greater than 24. Helical flutes 1220A, 1220B, 1220C, and 1220D each originate at the MxFD at separate locations that are equally spaced apart around the circumference of the shank 1211 or more specifically at 90° of separation. Each flute is continuous along the length of the cutting surface 1212 to the leading tip 1213.

With reference to FIG. 15D, it can be seen that flutes 1220A, 1220B, 1220C, and 1220D have an S-shaped splines 1221A, 1221B, 1221C, and 1221D. The flutes 1220A, 1220B, 1220C, and 1220D form helical cutting edges 1225A, 1225B, 1225C, and 1225D at the periphery of the shank 1211. With reference to FIG. 15D, a transverse cross-section is shown of the cutting portion 1212. The helical flutes 1220A, 1220B, 1220C, and 1220D cooperate to form a web or core 1226, which is generally square-shaped. The web or core is outlined by areas of radial clearance or cut outs created by splines 1221A, 1221B, 1221C, and 1221D. These areas of clearance are designated by numerals 1230A, 1230B, 1230C and 1230D. In transverse cross-section of the shank, splines 1221A, 1221B, 1221C, and 1221D of cutting flutes 1220A, 1220B, 1220C, and 1220D form teardrop clearance areas of variable depth. Clearance areas 1230A, 1230B, 1230C, and 1230D are circumscribed by cutting edges 1225A, 1225B, 1225C, and 1225D, or the perimeter of the shank, and the splines of the inner walls 1221A, 1221B, 1221C, and 1221D.

With further reference to FIG. 15D, it can be seen that splines 1221A, 1221B, 1221C, and 1221D intersect the periphery of the shank 1211 at point 1231A, 1231B, 1231C, and 1231D, respectively. These intersections are equal distances apart or at 90° of separation, forming a neutral angles (90° angle to the tangent of the perimeter of shank 1211) or slightly positive cutting angles (greater than 90° to the tangent of the perimeter of the shank 1211). Lines drawn connecting point 1231A, 1231B, 1231C, and 1231D form a square.

The splines 1221A, 1221B, 1221C, and 1221D are S-shaped and are individually symmetrical. The bisector of each spline divides the spline equally into convex and a concave segments which form the S-shaped curve. The lines that bisect each spline can be drawn to the center of the core 1226 and are equal in length. Further, an alternate bisector a can be drawn from the center of each spline through the greatest concavity the opposite spline and is also equal in length.

The greatest depth of each spline can be defined by a segment of a. These depths can vary and, furthermore, be calculated as a percentage of the length of a. The greatest depths of splines 1221A and 1221C, indicated with demarcated line segments 1237A and 1237C, are 5% of the length of a. The greatest depth of splines 1221B and 1221D, indicated with line segments 1237B and 1237D, are 25% of a. The greatest convexities of splines 1221A, 1221B, 1221C, and 1221D are mirror images of the greatest concavities of the same splines. The depth and height of each spline can vary; however, the cross sectional diameter of the core portion 1226 should generally not be narrower than approximately half or fifty percent of the cross sectional diameter of the shank of the instrument.

FIGS. 16A–16E illustrate another implementation, which is four sided or rectagonal in transverse cross-section and can be utilized to remove tissue and/or dentin from an ECS. The instrument includes a shank 311 similar to the one described above with respect to FIGS. 13A–13E and a working portion 312, which is tapered in a shank-to-tip direction. The tip 313 can include a cutting surface, which is confluent the working surface 312 (for example, like the tip shown in FIGS. 14A–14D). Alternatively, the tip 313 can display a non-cutting surface, which is confluent with the working portion 312 (for example, like the tip shown in FIG. 9C). The instrument includes an MxFD 317 and an MnFD 316. The shank 311 above the above the working portion 312 is essentially cylindrical exhibiting a slightly smaller diameter than the cutting surface at the MxFD. The shank here is similar to the one described in FIGS. 13A–13E. The instrument includes a modified or rolled edge portion 314, which is confluent with the cutting surface 312. This rolled-edge feature is illustrated in FIGS. 9A–9D. A fitting, which is suitable for an engine driven motor with a hand-piece and chuck or a handle utilized for manual instrumentation, is attached to the shank at its most proximal end also similar to the fitting described in FIGS. 13A–13E.

As shown in FIGS. 16A–16E, four continuous flutes 320A, 320B, 320C and 320D are substantially concave grooves, which follow the circumference of the working surface 312 spiraling toward the leading tip 313 forming concentric circles, which may be equidistant or become increasingly tighter or more numerous as they approach the tip. The total number of flutes from MxFD to the MnFD should be no fewer than 16 but not greater than 24. Flutes 320A, 320B, 320C, and 320D each originate at the MxFD at various locations spaced around the circumference of the shank, more specifically at 80°, 100°, 80°, and 100° of separation, respectively. Each flute is continuous along the length of the cutting surface 312 to the leading tip 313.

With reference to FIG. 16E, it can be seen that flutes 320A, 320B, 320C, and 320D have an S-shaped splines 321A, 321B, 321C, and 321D. The flutes 320A, 320B, 320C, and 320D form helical cutting edges 325A, 325B, 325C, and 325D at the periphery of the shank 311. As shown in FIG. 16E, a transverse cross-section is shown of the cutting portion 312. The flutes 320A, 320B, 320C, and 320D cooperate to form a web or core 326, which is essentially rectagonally shaped. The web or core is outlined by areas of radial clearance or cut outs created by the splines 321A, 321B, 321C, and 321D. These areas of clearance are designated by numerals 330A, 330B, 330C, and 330D. In transverse cross-section of the shank, the splines 321A, 321B, 321C, and 321D of flutes 320A, 320B, 320C, and 320D form teardrop clearance areas of variable depth. Clearance areas 330A, 330B, 330C, and 330D are circumscribed by cutting edges 325A, 325B, 325C, and 325D, or the perimeter of the shank, and the splines 321A, 321B, 321C, and 321D.

As shown in FIG. 16E, it can be seen that splines 321A, 321B, 321C, and 321D intersects the periphery of the shank 311 at points 331A, 331B, 331C, and 331D, respectively. These intersections are at 80°, 100°, 80°, and 100° of separation, respectively, forming neutral or slightly positive cutting angles. Lines drawn connecting point 331A, 331B, 331C, and 331D form a rectangle. The difference in degrees between the longest spline and the shortest spline is 20°. Alternatively, as shown in FIG. 16D, points 331A, 331B, 331C, and 331D can intersect the periphery of the shank at 90°, 95°, 80° and 95° of separation, respectively. Lines drawn connecting the point 331A, 331B, 331C, and 331D also form a rectangle. The outline of the trapezoid that is formed connecting point 331A, 331B, 331C, and 331D can vary. The difference in the number of degrees of separation between the longest spline and the short spline should not be less than 5° and not greater than 70°.

The splines 321A, 321B, 321C, and 321D are S-shaped and are individually symmetrical. The bisector of each spline divides the spline equally into convex and a concave segments which form the S-shaped curve. Alternate bisectors a and b can be drawn from the center of each spline through the greatest concavity the opposite spline.

The greatest depth of each spline can be defined segments of a and b. These depths can vary and, furthermore, be calculated as a percentage of the length of a and b. The greatest depths of splines 321A and 321C, indicated with demarcated line segments 337A and 337C, are 5% of the length of a. The greatest depth 321B and 321D, indicated with demarcated line segments 337B and 337D, are 5% of b. The greatest convexities of splines 321A, 321B, 321C, and 321D are mirror images of the greatest concavities of the same splines. The depth and height of each spline can vary; however, the cross sectional diameter of the core portion 326 should generally not be narrower than half or fifty percent of the cross sectional diameter of the shank of the instrument.

FIGS. 17A–17E illustrate another implementation, which is four sided and trapezoidal in transverse cross-section and can be utilized to remove tissue and/or dentin from an ECS. The instrument includes a shank 411 similar to the one described above with respect to FIGS. 13A–13E and a working portion 412, which is tapered in a shank-to-tip direction. The tip 413 can include a cutting surface, which is confluent the working surface 412 (for example, like the tip shown in FIGS. 14A–14D). Alternatively, the tip 413 can display a non-cutting surface, which is confluent with the working portion 412 (for example, like the tip shown in FIG. 9C). The instrument includes an MxFD 417 and an MnFD 416. The shank 411 above the above the working portion 412 is essentially cylindrical exhibiting a slightly smaller diameter than the cutting surface at the MxFD. The shank here is similar to the one described in FIGS. 13A–13E. The instrument includes a modified or rolled edge portion 414, which is confluent with the cutting surface 412. This rolled-edge feature is illustrated in FIGS. 9A–9D. A fitting, which is suitable for an engine driven motor with a hand-piece and chuck or a handle utilized for manual instrumentation, is attached to the shank at its most proximal end also similar to the fitting described in FIGS. 13A–13E.

As shown in FIGS. 17A–17E, four continuous flutes 420A, 420B, 420C and 420D are substantially concave grooves, which follow the circumference of the working surface 412 spiraling toward the leading tip 413 forming concentric circles, which may be equidistant or become increasingly tighter or more numerous as they approach the tip. The total number of flutes from MxFD to the MnFD should be no fewer than 16 but not greater than 24. Flutes 420A, 420B, 40C, and 420D each originate at the MxFD at various locations spaced around the circumference of the shank, more specifically at 90°, 100°, 70°, and 100° of separation, respectively. Each flute is continuous along the length of the cutting surface 412 to the leading tip 413.

With reference to FIG. 17E, it can be seen that flutes 420A, 420B, 420C, and 420D have an S-shaped splines 421A, 421B, 421C, and 421D. The flutes 420A, 420B, 420C, and 420D form helical cutting edges 425A, 425B, 425C, and 425D at the periphery of the shank 411. As shown in FIG. 17E, a transverse cross-section is shown of the cutting portion 412. The flutes 420A, 420B, 420C, and 420D cooperate to form a web or core 426, which is essentially rectagonally shaped. The web or core is outlined by areas of radial clearance or cut outs created by the splines 421A, 421B, 421C, and 421D. These areas of clearance are designated by numerals 430A, 430B, 430C, and 430D. In transverse cross-section of the shank, the splines 421A, 421B, 421C, and 421D of flutes 420A, 420B, 420C, and 420D form teardrop clearance areas of variable depth. Clearance areas 430A, 430B, 430C, and 430D are circumscribed by cutting edges 425A, 425B, 425C, and 425D, or the perimeter of the shank, and the splines 421A, 421B, 421C, and 421D.

As shown in FIG. 17E, it can be seen that splines 421A, 421B, 421C, and 421D intersects the periphery of the shank 411 at points 431A, 431B, 431C, and 431D, respectively. These intersections are at 90°, 100°, 70°, and 100° of separation, respectively, forming neutral or slightly positive cutting angles. Lines drawn connecting point 331A, 331B, 331C, and 331D form a trapezoid. The difference in degrees between the longest spline and the shortest spline is 30°. Alternatively, as shown in FIG. 16D, points 331A, 331B, 331C, and 331D can intersect the periphery of the shank at 90°, 95°, 80° and 95° of separation, respectively. Lines drawn connecting the point 431A, 431B, 431C, and 431D also form a trapezoid. The outline of the trapezoid that is formed connecting point 431A, 431B, 431C, and 431D can vary. The difference in the number of degrees of separation between the longest spline and the short spline should not be less than 50 and not greater than 70°.

The splines 421A, 421B, 421C, and 421D are S-shaped and are individually symmetrical. The bisector of each spline divides the spline equally into convex and a concave segments which form the S-shaped curve. Alternate bisectors a, b, and c can be drawn from the center of each spline through the greatest concavity the opposite spline.

The greatest depth of each spline can be defined as segments of a, b, and c. These depths can vary and, furthermore, be calculated as a percentage of the length of a, b, and c. The greatest depths of splines 421A, indicated with demarcated line segments 437A, is 5% of the length of a. The greatest depth 421B, 421C, and 421D can be similarly indicated. The greatest convexities of splines 421A, 421B, 421C, and 421D are mirror images of the greatest concavities of the same splines. The depth and height of each spline can vary; however, the cross sectional diameter of the core portion 426 should generally not be narrower than half or fifty percent of the cross sectional diameter of the shank of the instrument.

Alternatives

A number of implementations of the invention have been described. Nevertheless, it will be understood that various modifications may be made without departing from the spirit and scope of the invention. For example, in other implementations, similar instruments can include 5 or 6 flutes. The shanks and/or metal blanks from which these instruments can be fabricated and have slightly larger diameters providing enough material to facilitate the increased number of flutes. The flutes, therefore, would require fewer spirals per unit length. Instruments of increasing size, or diameter, become increasingly less flexible. Implementing more flutes and/or cutting the flutes deeper into the metal blanks during manufacture can facilitate compensation for the decrease in flexibility. In addition, wider and deeper spaces also provide greater opportunity to haul out debris from the apex to the coronal aspect of the tooth. Accordingly, other embodiments are within the scope of the following claims.

What is claimed is:

1. A set of endodontic instruments for preparing an endodontic cavity space, the set comprising:
  a first endodontic instrument;
  a second endodontic instrument; and
  a third endodontic instrument, each endodontic instrument including a working portion that has a cone-like shape, each working portion having an effective contact area defined by the exposed surface area of the working portion's respective cone-like shape, the difference between the effective contact areas of the first endodontic instrument and second endodontic instrument being substantially the same as the difference between the effective contact areas of the second endodontic instrument and third endodontic instrument.

2. The set of claim 1, further comprising:
  a fourth endodontic instrument;
  a fifth endodontic instrument;
  a sixth endodontic instrument, the difference between the effective contact areas of the third and fourth endodontic instruments being substantially the same as the difference between the effective contact areas of the fourth and fifth endodontic instruments and also as the difference between the effective contact areas of the fifth and sixth endodontic instruments.

3. The set of claim 1, wherein:
  at least one of the instruments includes a cross section that is asymmetrical.

4. The set of claim 3, wherein:
  at least one of the instruments includes a quadrilateral cross section.

5. The set of claim 4, wherein:

at least one of the instruments includes a trapezoidal cross section.

6. The set of claim 3, wherein:

at least one of the instruments includes a triangular cross section.

7. The set of claim 1, wherein:

at least one of the instruments includes a square cross section.

8. The set of claim 1, wherein:

at least one of the instruments is made of Nickel Titanium, includes a center of mass that is off the longitudinal axis, and is configured to swagger when rotated at operational speeds about the longitudinal axis.

9. The set of claim 1, wherein:

at least one of the instruments includes a reversed helix.

10. The set of claim 1, wherein:

at least one of the instruments includes flutes having cross cuts.

11. The set of claim 1, wherein:

at least one of the instruments includes flutes having rolled edges, whereby the flutes are operable to haul but not cut.

12. The set of claim 1, wherein:

at least one of the instruments includes S-shaped splines.

13. The set of claim 1, wherein:

the instruments are operable for preparing a curved endodontic cavity space.

14. The set of claim 1, wherein:

the instruments are operable for preparing a straight endodontic cavity space.

15. A set of endodontic instruments for preparing an endodontic cavity space, the set comprising:

a first endodontic instrument;

a second endodontic instrument; and a third endodontic instrument, wherein each endodontic instrument has a longitudinal axis, wherein each endodontic instrument has a cross sectional area at a predetermined point on its longitudinal axis, the predetermined point being the same for the endodontic instruments of the set; and wherein the difference between the cross sectional areas of the first and second endodontic instruments is substantially the same as the difference between the cross sectional areas of the second and third endodontic instruments.

16. The set of claim 15, wherein:

the predetermined point is at substantially the same depth as the fulcrum of an endodontic cavity space when the instrument is fully inserted in to the endodontic cavity space.

17. The set of claim 15, wherein:

the predetermined point is 6 millimeters away from the tip.

18. The set of claim 15, wherein:

one of the instruments of the set has a center of mass that is off the rotation of axis of the drill bit, wherein the drill bit is made of NiTi, and wherein the drill bit is operable to swagger when rotated at operational speeds about the axis of rotation.

19. The set of claim 15, wherein:

one of the instruments includes a reversed helix.

* * * * *

UNITED STATES PATENT AND TRADEMARK OFFICE
CERTIFICATE OF CORRECTION

PATENT NO. : 6,942,484 B2 Page 1 of 1
DATED : September 13, 2005
INVENTOR(S) : Michael J. Scianamblo, D.D.S.

It is certified that error appears in the above-identified patent and that said Letters Patent is hereby corrected as shown below:

Column 22,
Line 54, replace "a fifth endodontic instrument;" with -- a fifth endodontic instrument; and --.

Signed and Sealed this

Twenty-fifth Day of April, 2006

JON W. DUDAS
*Director of the United States Patent and Trademark Office*